(12) United States Patent
Kanai et al.

(10) Patent No.: US 7,736,051 B2
(45) Date of Patent: Jun. 15, 2010

(54) THERMOELECTRIC DEVICE AND MIRROR SURFACE STATE DETECTION DEVICE

(75) Inventors: Yoshiyuki Kanai, Tokyo (JP); Kazumasa Ibata, Tokyo (JP); Shigeki Shoji, Tokyo (JP); Masaki Takechi, Tokyo (JP); Zentaro Nakamura, Tokyo (JP); Masahiro Komatsu, Tokyo (JP); Ken Iwakiri, Tokyo (JP); Ryu Akimoto, Tokyo (JP); Shingo Masumoto, Tokyo (JP)

(73) Assignee: Yamatake Corporation, Tokyo (JP)

( * ) Notice: Subject to any disclaimer, the term of this patent is extended or adjusted under 35 U.S.C. 154(b) by 1477 days.

(21) Appl. No.: 11/097,696

(22) Filed: Mar. 30, 2005

(65) Prior Publication Data

US 2005/0220167 A1 Oct. 6, 2005

(30) Foreign Application Priority Data

| Mar. 30, 2004 | (JP) | ............................. 2004-101403 |
| Mar. 30, 2004 | (JP) | ............................. 2004-101423 |
| Oct. 20, 2004 | (JP) | ............................. 2004-317086 |
| Feb. 14, 2005 | (JP) | ............................. 2005-035525 |

(51) Int. Cl.
*G01N 25/00* (2006.01)
*G01J 5/00* (2006.01)
*G01K 1/00* (2006.01)

(52) U.S. Cl. .............................. 374/16; 374/20; 374/28; 374/131; 374/121

(58) Field of Classification Search .................... 374/16, 374/28, 20, 131, 121
See application file for complete search history.

(56) References Cited

U.S. PATENT DOCUMENTS 5,088,833 A * 2/1992 Tsang et al. .................. 374/17

FOREIGN PATENT DOCUMENTS

| JP | 41-18557 | 8/1941 |
| JP | U57-101952 | 6/1982 |
| JP | 58-062253 | 4/1983 |
| JP | 58-113840 | 7/1983 |
| JP | 59-170754 | 9/1984 |
| JP | 61-75235 | 4/1986 |
| JP | 61-075235 A | 4/1986 |
| JP | 61-120050 | 6/1986 |
| JP | 62-032348 | 2/1987 |
| JP | U62-126760 | 8/1987 |
| JP | 63-308846 | 12/1988 |

(Continued)

OTHER PUBLICATIONS

"The Outline of Industrial Measurement Technology 10, Temperature/Moisture Measurement", Nikkan Kogyo Shimbun, pp. 87-91, Abstract.

*Primary Examiner*—Gail Verbitsky
*Assistant Examiner*—Mirellys Jagan
(74) *Attorney, Agent, or Firm*—Blakely, Sokoloff, Taylor & Zafman LLP

(57) ABSTRACT

In a thermoelectric device, a thermoelectric element has one surface on a low temperature side and the other surface on a high temperature side. A member is attached to at least one of the low- and high-temperature-side surfaces of the thermoelectric element. A temperature detection element is provided between the member and the surface of the thermoelectric element to which the member is attached. A mirror surface state detection device is also disclosed.

3 Claims, 19 Drawing Sheets

FOREIGN PATENT DOCUMENTS

| | | |
|---|---|---|
| JP | 63-309846 A | 12/1988 |
| JP | 64-057589 | 3/1989 |
| JP | 1-156451 | 10/1989 |
| JP | 02-162240 | 6/1990 |
| JP | 04-034674 A | 2/1992 |
| JP | 4-41655 U | 4/1992 |
| JP | 04-370774 | 12/1992 |
| JP | 7-181131 | 7/1995 |
| JP | 07-104304 B2 | 11/1995 |
| JP | 07-325055 | 12/1995 |
| JP | 08-094449 | 4/1996 |
| JP | 09-307030 | 11/1997 |
| JP | 2000-180357 | 6/2000 |
| JP | 2001-028385 | 1/2001 |
| JP | 2001-330576 | 11/2001 |
| JP | 2002-014065 | 1/2002 |
| JP | 2002-176009 | 6/2002 |
| JP | 2003-57168 | 2/2003 |
| JP | 2005-283510 A | 10/2005 |
| JP | 2005-291889 | 10/2005 |
| WO | WO 9201927 A1 * | 2/1992 |
| WO | WO 03/014719 A1 | 2/2003 |
| WO | WO 03/044509 | 5/2003 |

* cited by examiner

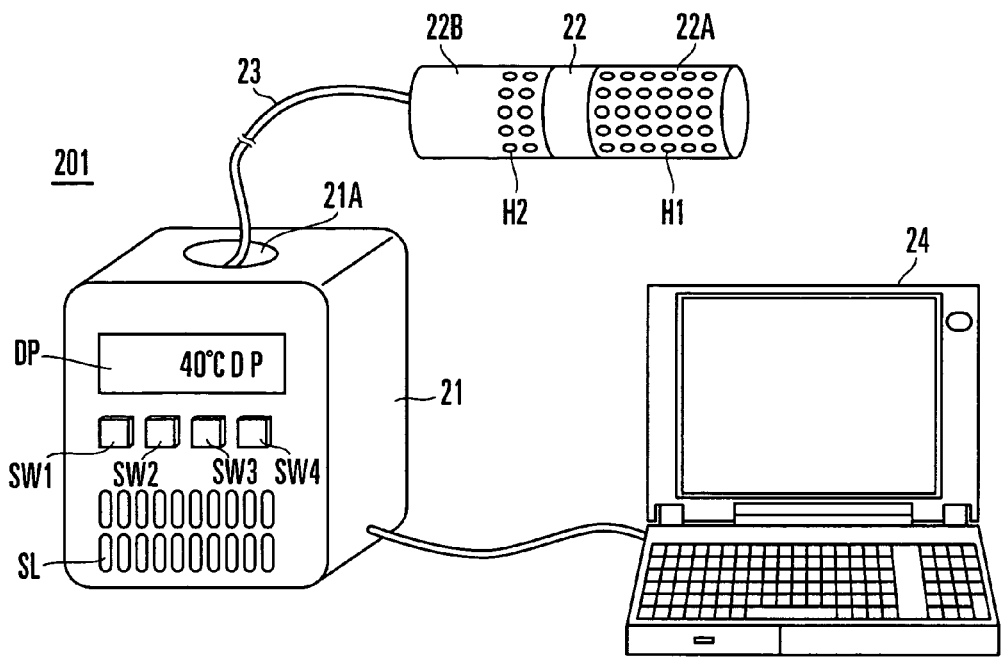
F I G. 6
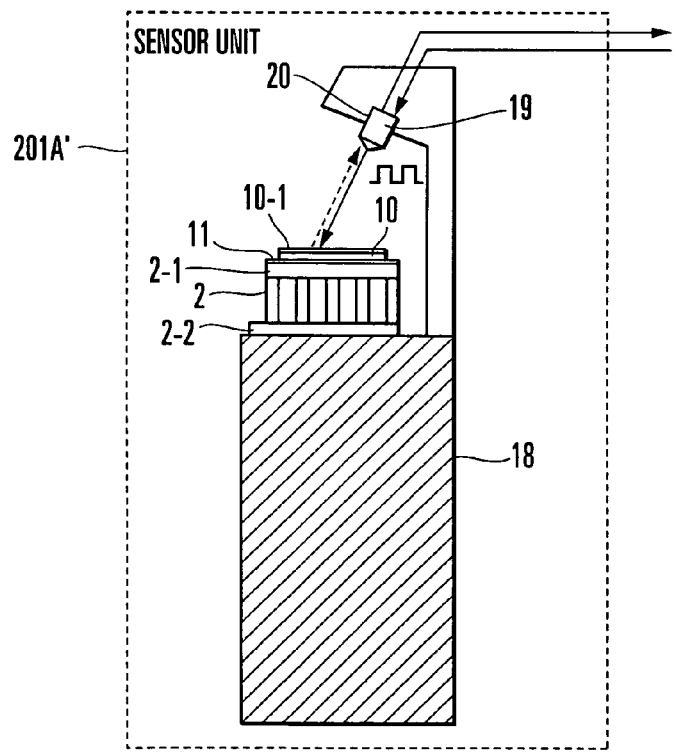
F I G. 7

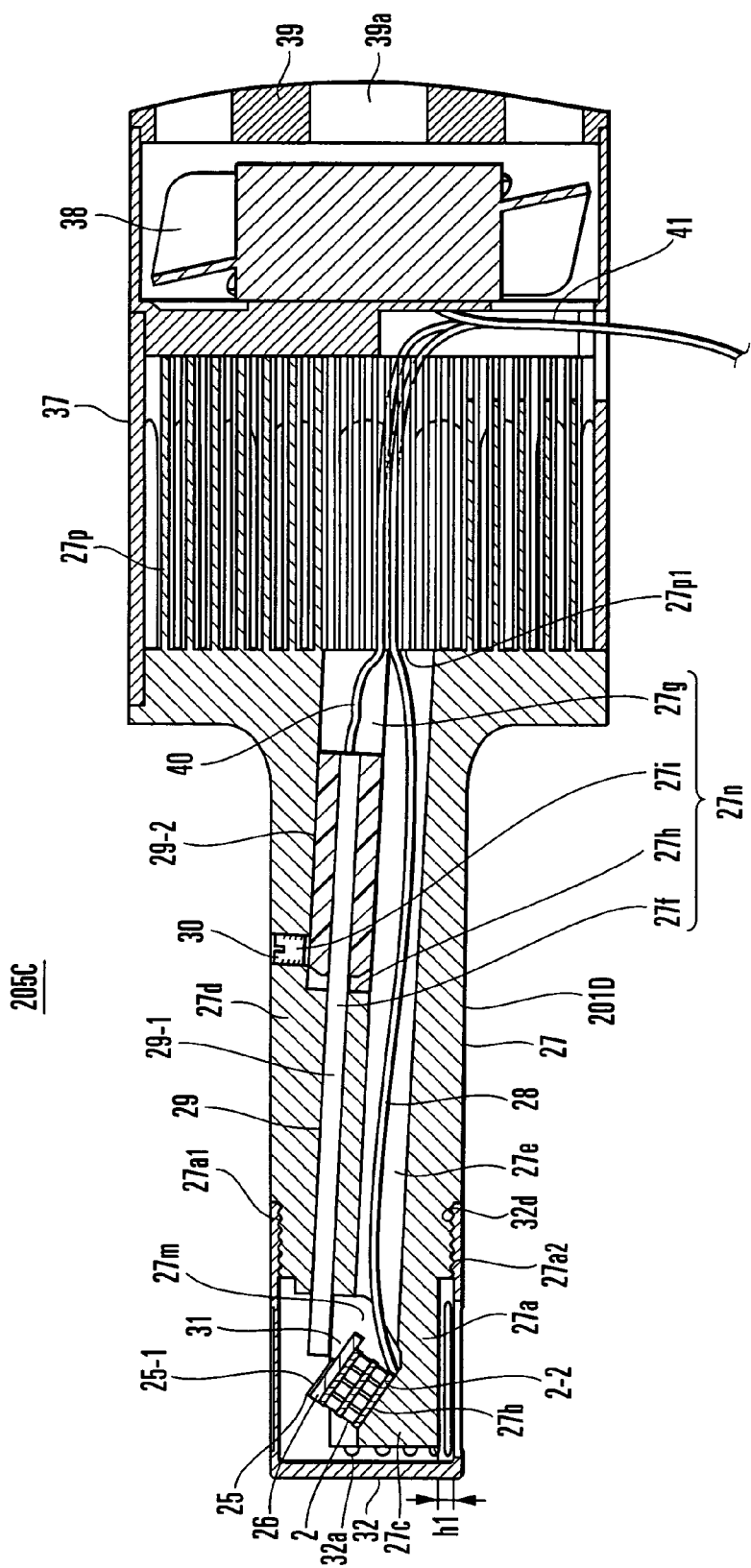
F I G. 23

THERMOELECTRIC DEVICE AND MIRROR SURFACE STATE DETECTION DEVICE

BACKGROUND OF THE INVENTION

The present invention relates to a thermoelectric device which cools or heats a member by using a thermoelectric element having one surface on the low temperature side and the other surface on the high temperature side.

Conventionally, as a humidity measuring method, a dew point detection method is known, in which the temperature of a target measurement gas is decreased, and the temperature at which vapor contained in the target measurement gas partially condenses is measured, thereby detecting the dew point. For example, reference 1 ("The Outline of Industrial Measurement Technology 10, Temperature/Moisture Measurement", Nikkan Kogyo Shimbun, PP. 87-91) describes a mirror surface cooling dew point detector which cools a mirror by using a freezing mixture, refrigerator, or electronic cooler, detects a change in intensity of reflected light on the mirror surface of the cooled mirror, and measures the temperature of the mirror surface at this time, thereby detecting the dew point of moisture in the target measurement gas.

Mirror surface cooling dew point detectors are classified into two types depending on the type of reflected light to be used. One type uses a regular-reflected light detection method using regular-reflected light described in reference 2 (Japanese Patent Laid-Open No. 61-75235). The other type uses a scattered light detection method using scattered light described in reference 3 (Japanese Patent Laid-Open No. 63-309846).

[Regular-Reflected Light Detection Method]

FIG. 26 shows the main part of a conventional mirror surface cooling dew point detector which employs the regular-reflected light detection method. A mirror surface cooling dew point detector 101 comprises a chamber 1 in which a target measurement gas flows and a thermoelectric cooling element (Peltier element) 2 provided in the chamber 1. A bolt 4 is attached to a cooled surface 2-1 of the thermoelectric cooling element 2 through a copper block 3. A radiating fin 5 is attached to a heated surface 2-2 of the thermoelectric cooling element 2. An upper surface 4-1 of the bolt 4 attached to the copper block 3 is a mirror surface. A hole is formed in the side surface of the copper block 3. A wire-wound resistance thermometer sensor (temperature detection element) 6 is embedded in this hole through silicone grease (FIG. 28). A light-emitting element 7 which obliquely irradiates the upper surface (mirror surface) 4-1 of the bolt 4 with light and a light-receiving element 8 which receives the regular-reflected light of light emitted from the light-emitting element 7 to the mirror surface 4-1 are provided at the upper portion of the chamber 1.

In the mirror surface cooling dew point detector 101, the mirror surface 4-1 in the chamber 1 is exposed to the target measurement gas flowing into the chamber 1. If no condensation occurs on the mirror surface 4-1, the light emitted from the light-emitting element 7 is almost wholly regularly reflected and received by the light-receiving element 8. Hence, when no condensation occurs on the mirror surface 4-1, the intensity of reflected light received by the light-receiving element 8 is high.

As the current to the thermoelectric cooling element 2 is increased to lower the temperature of the cooled surface 2-1 of the thermoelectric cooling element 2, vapor contained in the target measurement gas condenses on the mirror surface 4-1. The light emitted from the light-emitting element 7 is partially absorbed or diffused by the molecules of water. The intensity of the reflected light (regular-reflected light) received by the light-receiving element 8 decreases. When the change in regular-reflected light on the mirror surface 4-1 is detected, the change of the state on the mirror surface 4-1, i.e., adhesion of moisture (water droplets) on the mirror surface 4-1 can be recognized. In addition, when the temperature of the mirror surface 4-1 at this time is measured indirectly by the temperature detection element 6, the dew point of moisture in the target measurement gas can be detected.

[Scattered Light Detection Method]

FIG. 27 shows the main part of another conventional mirror surface cooling dew point detector which employs the scattered light detection method. A mirror surface cooling dew point detector 102 has almost the same arrangement as the mirror surface cooling dew point detector 101 using the regular-reflected light detection method except the mount position of the light-receiving element 8. In the mirror surface cooling dew point detector 102, the light-receiving element 8 is provided not at the position to receive the regular-reflected light of light emitted from the light-emitting element 7 to the mirror surface 4-1 but at the position to receive scattered light.

In the mirror surface cooling dew point detector 102, the mirror surface 4-1 is exposed to the target measurement gas flowing into the chamber 1. If no condensation occurs on the mirror surface 4-1, the light emitted from the light-emitting element 7 is almost wholly regularly reflected, and the amount of light received by the light-receiving element 8 is very small. Hence, when no condensation occurs on the mirror surface 4-1, the intensity of reflected light received by the light-receiving element 8 is low.

As the current to the thermoelectric cooling element 2 is increased to lower the temperature of the cooled surface 2-1 of the thermoelectric cooling element 2, vapor contained in the target measurement gas condenses on the mirror surface 4-1. The light emitted from the light-emitting element 7 is partially absorbed or diffused by the molecules of water. The intensity of the diffused light (scattered light) received by the light-receiving element 8 increases. When the change in scattered light on the mirror surface 4-1 is detected, the change of the state on the mirror surface 4-1, i.e., adhesion of moisture (water droplets) on the mirror surface 4-1 can be recognized. In addition, when the temperature of the mirror surface 4-1 at this time is measured indirectly by the temperature detection element 6, the dew point of moisture in the target measurement gas can be detected.

In the above-described dew point detectors, condensation (moisture) on the mirror surface 4-1 is detected. With the same arrangement as described above, frost (moisture) on the mirror surface 4-1 can also be detected.

However, for the above-described conventional mirror surface cooling dew point detector 101 or 102, assembly is not easy because the temperature detection element 6 is embedded through the silicone grease in the hole formed in the side portion of the copper block 3. Since the temperature detection element 6 is covered with the silicone grease, the response is poor due to the thermal resistance by the silicone grease. The copper block 3 is inserted between the mirror surface 4-1 and the thermoelectric cooling element 2. With this structure, a temperature gradient which decreases the measurement accuracy may be generated. In addition, since the thermal capacity by the copper block 3 is large, and the response is poor. Since the copper block 3 is provided, the outer size of the sensor unit increases, and size reduction is difficult.

Reference 4 (Japanese Patent Laid-Open No. 9-307030) describes a cooling device which cools a heat-producing electronic device (e.g., CPU) by using a thermoelectric cooling element. In this cooling device, the CPU is attached to the cooled surface of the thermoelectric cooling element, and the temperature of the semiconductor element or cooling-side conductor of the thermoelectric cooling element is measured. More specifically, as shown in FIG. 29, a CPU (cooled member) 61 is attached to the cooled surface 2-1 of the thermoelectric cooling element 2. A temperature detection element 62 is attached to a column (semiconductor element) 2a of the thermoelectric cooling element 2 or a bottom surface 2b of the cooled surface (cooling-side conductor) 2-1 to indirectly measure the temperature of the CPU 61. An arrangement can be considered from the structure described in reference 4, in which a mirror 9 is attached to the cooled surface 2-1 of the thermoelectric cooling element 2, and the temperature detection element 62 measures the temperature of the column 2a of the thermoelectric cooling element 2 or the bottom surface 2b of the cooled surface 2-1, as shown in FIG. 30. In this structure, however, since a thermal resistance is generated in the bonding portion between the mirror 9 and the cooled surface 2-1 of the thermoelectric cooling element 2 and in the cooled surface 2-1 itself, the temperature of the mirror 9 cannot be detected accurately at a satisfactory response.

Although mirror surface cooling dew point detectors have been described above, this also applied to the conventional cooling device shown in FIG. 29. That is, the temperature of the CPU 61 cannot accurately be detected. As shown in FIG. 31, a member 63 is attached to the heated surface 2-2 of the thermoelectric cooling element 2 and heated. In this case, the thermoelectric cooling element 2 serves as a thermoelectric heating element so that not a cooling device but a heating device is formed. Even in this case, when the temperature of the column 2a of the thermoelectric heating element 2 or a bottom surface 2c of the heated surface 2-2 is measured, the temperature of a member (heated member) 30 cannot be detected accurately at a high response. The thermoelectric cooling element 2 will also be referred to as a thermoelectric heating element depending on its utilization form, and "thermoelectric element" will be used as a general term for the thermoelectric cooling element and thermoelectric heating element hereinafter.

SUMMARY OF THE INVENTION

The present invention has been made to solve the above-described problems, and has as its object to provide a thermoelectric device capable of measuring the temperature of a cooled member or heated member accurately at a high response.

In order to achieve the above object, according to the present invention, there is provided a thermoelectric device comprising a thermoelectric element which has one surface on a low temperature side and the other surface on a high temperature side, a member which is attached to at least one of the low-temperature-side surface and high-temperature-side surface of the thermoelectric element, and a temperature detection element which is provided between the member and the surface of the thermoelectric element to which the member is attached.

BRIEF DESCRIPTION OF THE DRAWINGS

FIG. 6 is a view showing a state in which a personal computer is connected to the control box;

FIG. 7 is a view showing a modification of the sensor unit of the mirror surface cooling dew point detector according to the first embodiment;

FIG. 23 is a schematic view showing the structure of a mirror surface cooling sensor (L-type mirror surface cooling sensor) in still another embodiment (fourth embodiment) of a mirror surface cooling dew point detector which uses a thermoelectric device according to the present invention;

DESCRIPTION OF THE PREFERRED EMBODIMENTS

The present invention will be described below in detail with reference to the accompanying drawings.

First Embodiment: Mirror Surface Cooling Dew Point Detector (Scattered Light Detection Method)

Figure 1:
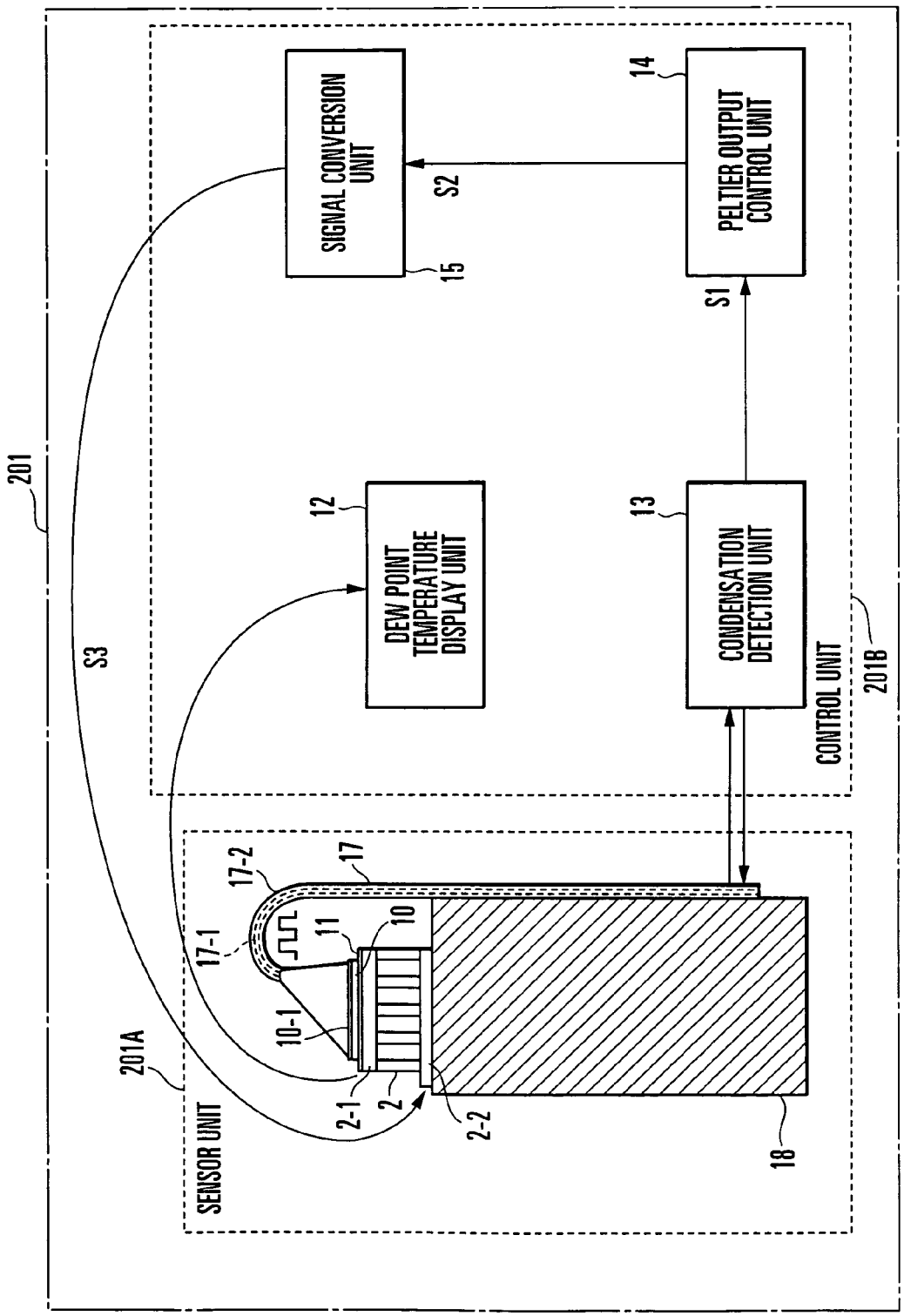
FIG. 1 is a schematic view showing an embodiment (first embodiment) of a mirror surface cooling dew point detector which uses a thermoelectric device according to the present invention.

FIG. 1 shows an embodiment of a mirror surface cooling dew point detector which uses a thermoelectric device according to the present invention. A mirror surface cooling dew point detector 201 has a sensor unit 201A and control unit 201B.

In the sensor unit 201A, a mirror 10 is attached to a cooled surface 2-1 of a thermoelectric cooling element (Peltier element) 2. The mirror 10 is formed from, e.g., a silicon chip whose surface 10-1 is a mirror surface. A thin-film resistance thermometer sensor (temperature detection element) 11 made of, e.g., platinum is formed between the mirror 10 and the cooled surface 2-1 of the thermoelectric cooling element 2. In this embodiment, the layer of the thin-film resistance thermometer sensor is formed on the entire cooled surface 2-1 of the thermoelectric cooling element 2 by using the semiconductor manufacturing technology. The mirror 10 is attached to the cooled surface 2-1 of the thermoelectric cooling element 2 having the layer of the thin-film resistance thermometer sensor. The layer of the thin-film resistance thermometer sensor may be formed on the lower surface of the mirror 10 by using the semiconductor manufacturing technology. The mirror 10 having the layer of the thin-film resistance thermometer sensor may be attached to the cooled surface 2-1 of the thermoelectric cooling element 2.

Figure 2A:
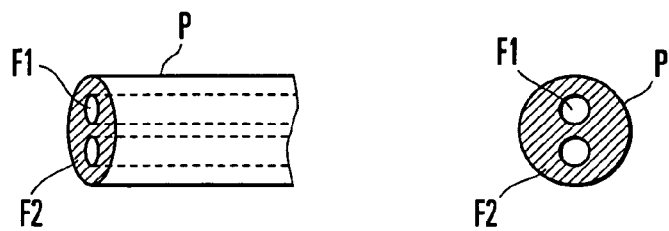
FIG. 2A is a view showing an arrangement in which a light-emitting-side optical fiber and light-receiving-side optical fiber are provided in one tube.
Figure 2B:
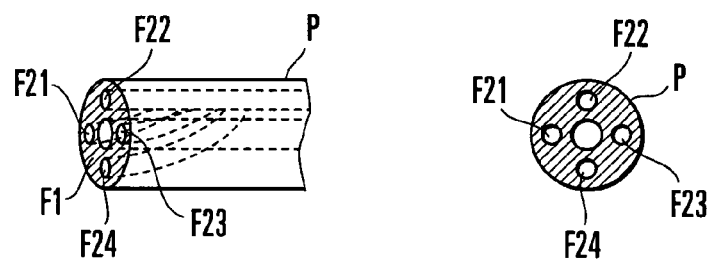
FIG. 2B is a view showing another arrangement in which a light-emitting-side optical fiber and light-receiving-side optical fiber are provided in one tube.
Figure 2C:
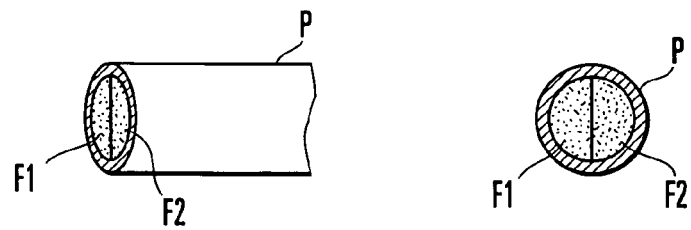
FIG. 2C is a view showing still another arrangement in which a light-emitting-side optical fiber and light-receiving-side optical fiber are provided in one tube.
Figure 2D:
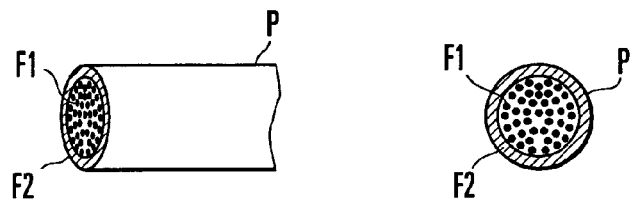
FIG. 2D is a view showing still another arrangement in which a light-emitting-side optical fiber and light-receiving-side optical fiber are provided in one tube.
Figure 2E:
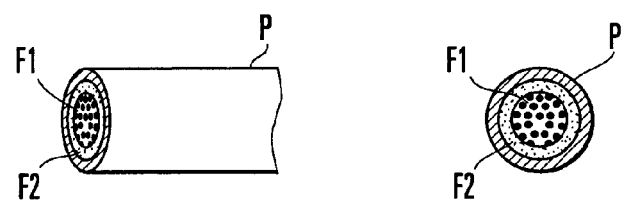
FIG. 2E is a view showing still another arrangement in which a light-emitting-side optical fiber and light-receiving-side optical fiber are provided in one tube.

In the sensor unit 201A, a cylindrical heat sink 18 is attached to a heated surface 2-2 of the thermoelectric cooling element 2. A tube (or cable) 17 with the upper end portion curved into a J-shape is provided along the heat sink 18. As the tube 17, various tubes P as shown in FIGS. 2A to 2E, which accommodate optical fibers, can be used. Referring to FIG. 2A, a light-emitting-side optical fiber F1 and light-receiving-side optical fiber F2 are parallel in the tube P. In the tube P, the space around the light-emitting-side optical fiber F1 and light-receiving-side optical fiber F2 is filled with a potting agent. Referring to FIG. 2B, the light-emitting-side (or light-receiving-side) optical fiber F1 and light-receiving-side (or light-emitting-side) optical fibers F21 to F24 arranged around the fiber F1 are provided in the tube P. Referring to FIG. 2C, the left half in the tube P is formed from the light-emitting-side optical fiber F1, and the right half is formed from the light-receiving-side optical fiber F2. Referring to FIG. 2D, the light-emitting-side optical fibers F1 and light-receiving-side optical fibers F2 are mixed in the tube P. Referring to FIG. 2E, the light-emitting-side (or light-receiving-side) optical fibers F1 are provided at the center of the tube P, and the light-receiving-side (or light-emitting-side) optical fiber F2 is arranged around the optical fibers F1.

In the mirror surface cooling dew point detector 201 shown in FIG. 1, the tube P shown in FIG. 2A is used as the tube 17. The tube 17 incorporates a light-emitting-side optical fiber 17-1 and light-receiving-side optical fiber 17-2. The distal end portions (light-emitting portion and light-receiving portion) of the light-emitting-side optical fiber 17-1 and light-receiving-side optical fiber 17-2, which are curved into a J-shape, are directed to the mirror surface 10-1 of the mirror 10 and tilted at a predetermined tilt angle with respect to the mirror surface 10-1. As a result, the light irradiation direction (optical axis) from the optical fiber 17-1 and the light-receiving direction (optical axis) on the optical fiber 17-2 are parallel. The optical fibers are arranged adjacent at the same tilt angle.

The control unit 201B includes a dew point temperature display unit 12, condensation detection unit 13, Peltier output control unit 14, and signal conversion unit 15. The temperature of the mirror 10 detected by the temperature detection element 11 is displayed on the dew point temperature display unit 12. The condensation detection unit 13 causes the optical fiber 17-1 to obliquely irradiate the mirror surface 10-1 of the mirror 10 with pulse light from the tip at a predetermined period. The condensation detection unit 13 also obtains the difference between the upper limit value and lower limit value of reflected pulse light (scattered light) received through the optical fiber 17-2 as the intensity of the reflected pulse light and sends a signal S1 corresponding to the reflected pulse light intensity to the Peltier output control unit 14. Upon receiving the signal S1 from the condensation detection unit 13, the Peltier output control unit 14 compares the reflected pulse light intensity with a predetermined threshold value. If the reflected pulse light intensity is less than the threshold value, the Peltier output control unit 14 outputs, to the signal conversion unit 15, a control signal S2 to increase the current to the thermoelectric cooling element 2 in accordance with the value of the signal S1. If the reflected pulse light intensity exceeds the threshold value, the Peltier output control unit 14 outputs, to the signal conversion unit 15, the control signal S2 to decrease the current to the thermoelectric cooling element 2 in accordance with the value of the signal S1. The signal conversion unit 15 supplies, to the thermoelectric cooling element 2, a current S3 indicated by the control signal S2 from the Peltier output control unit 14.

Figure 3A:
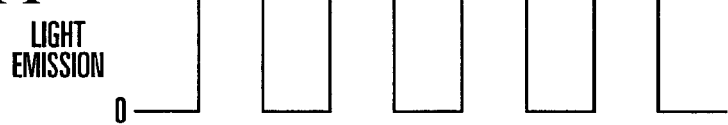
FIG. 3A is a graph showing the waveform of pulse light with which the mirror surface is irradiated.

In the mirror surface cooling dew point detector 201, the sensor unit 201A is placed in the target measurement gas. The condensation detection unit 13 causes the optical fiber 17-1 to obliquely irradiate the mirror surface 10-1 of the mirror 10 with pulse light from the tip at a predetermined period (FIG. 3A). The mirror surface 10-1 is exposed to the target measurement gas. If no condensation occurs on the mirror surface 10-1, pulse light emitted from the tip of the optical fiber 17-1 is almost wholly regularly reflected, and the amount of reflected pulse light (scattered light) received from the mirror surface 10-1 through the optical fiber 17-2 is very small. Hence, when no condensation occurs on the mirror surface 10-1, the intensity of reflected pulse light received through the optical fiber 17-2 is low.

The condensation detection unit 13 obtains the difference between the upper limit value and lower limit value of reflected pulse light received through the optical fiber 17-2 as the intensity of the reflected pulse light and sends the signal S1 corresponding to the reflected pulse light intensity to the Peltier output control unit 14. In this case, the reflected pulse light intensity is almost zero and less than the threshold value. For this reason, the Peltier output control unit 14 sends, to the signal conversion unit 15, the control signal S2 to increase the current to the thermoelectric cooling element 2. With this operation, the current S3 from the signal conversion unit 15 to the thermoelectric cooling element 2 increases, and the temperature of the cooled surface 2-1 of the thermoelectric cooling element 2 becomes low.

As the temperature of the cooled surface 2-1 of the thermoelectric cooling element 2, i.e., the temperature of the mirror 10 is decreased, vapor contained in the target measurement gas condenses on the mirror surface 10-1 of the mirror 10. The pulse light emitted from the tip of the optical fiber 17-1 is partially absorbed or diffused by the molecules of water. The intensity of the reflected pulse light (scattered light) received from the mirror surface 10-1 through the optical fiber 17-2 increases.

Figure 3B:
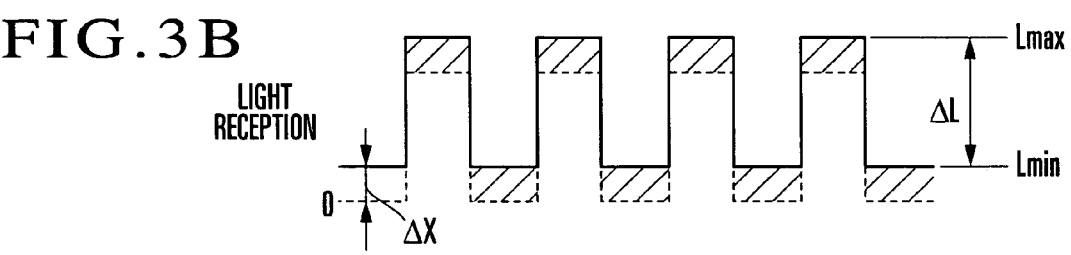
FIG. 3B is a graph showing the waveform of reflected pulse light received from the mirror surface.

The condensation detection unit 13 obtains the difference between the upper limit value and lower limit value of each pulse of the received reflected pulse light as the intensity of the reflected pulse light. More specifically, as shown in FIG. 3B, a difference ΔL between an upper limit value Lmax and lower limit value Lmin of one pulse of the reflected pulse light is obtained as the intensity of the reflected pulse light. By the processing by the condensation detection unit 13, disturbance light ΔX contained in the reflected pulse light is removed. Hence, any operation error by disturbance light can be prevented. The processing scheme by the condensation detection unit 13 using pulse light to prevent any operation error by disturbance light is called a pulse modulation scheme. With this processing, the chamber of the sensor unit 202A can be omitted from the mirror surface cooling dew point detector 201.

When the intensity of the reflected pulse light received through the optical fiber 17-2 exceeds the threshold value, the Peltier output control unit 14 sends, to the signal conversion unit 15, the control signal S2 to decrease the current to the thermoelectric cooling element 2. With this operation, the decrease in temperature of the cooled surface 2-1 of the thermoelectric cooling element 2 is suppressed, and condensation is suppressed. When condensation is suppressed, the intensity of the reflected pulse light received through the optical fiber 17-2 becomes low. When the reflected pulse light intensity is less than the threshold value, the Peltier output control unit 14 sends, to the signal conversion unit 15, the control signal S2 to increase the current to the thermoelectric cooling element 2. By repeating this operation, the temperature of the cooled surface 2-1 of the thermoelectric cooling element 2 is adjusted so that the intensity of reflected pulse light received through the optical fiber 17-2 almost equals the threshold value. The adjusted temperature, i.e., the temperature (dew point temperature) at which condensation which has occurred on the mirror surface 10-1 reaches the equilibrium state is displayed on the dew point temperature display unit 12 as the dew point temperature.

In the mirror surface cooling dew point detector 201, the temperature detection element 11 is provided between the mirror 10 and the cooled surface 2-1 of the thermoelectric cooling element 2. For this reason, the thermal resistance is low so that the temperature of the mirror 10 can be measured accurately at a high response. Hence, the dew point temperature measurement accuracy increases, and the response also increases.

The mirror surface cooling dew point detector 201 requires no copper block 3 (FIG. 28), unlike the prior art. Since the temperature detection element 6 need not be attached to the copper block 3, size reduction can be implemented by integrating the thermoelectric cooling element 2 and mirror 10. In addition, assembly is easy, the number of components can be decreased, and the cost can be reduced.

In the mirror surface cooling dew point detector 201, the light-emitting-side optical fiber 17-1 and light-receiving-side optical fiber 17-2 are attached to one point. This contributes to size reduction of the detection unit 201A. In addition, the light-emitting-side optical fiber 17-1 and light-receiving-side optical fiber 17-2 are accommodated in the tube 17. Hence, no alignment is necessary between the light-emitting-side optical fiber 17-1 and light-receiving-side optical fiber 17-2, resulting in high workability in assembly.

In the mirror surface cooling dew point detector 201, the sensor unit 202A has no chamber, and the suction pump or suction tube to draw the target measurement gas into the chamber, the exhaust tube, and the flowmeter can be omitted. For this reason, the number of components is decreased, the sensor unit 201A can be made more compact, assembly is easy, and the cost can be reduced. Since none of the suction pump, suction tube, exhaust tube, and flowmeter need be arranged, the detector can easily be installed in the measurement atmosphere. Since the sensor unit 201A need have none of the suction pump, suction tube, exhaust tube, and flowmeter, and the detector includes only two components, i.e., the sensor unit 201A and control unit 201B, the detector can easily be carried.

Figure 4:
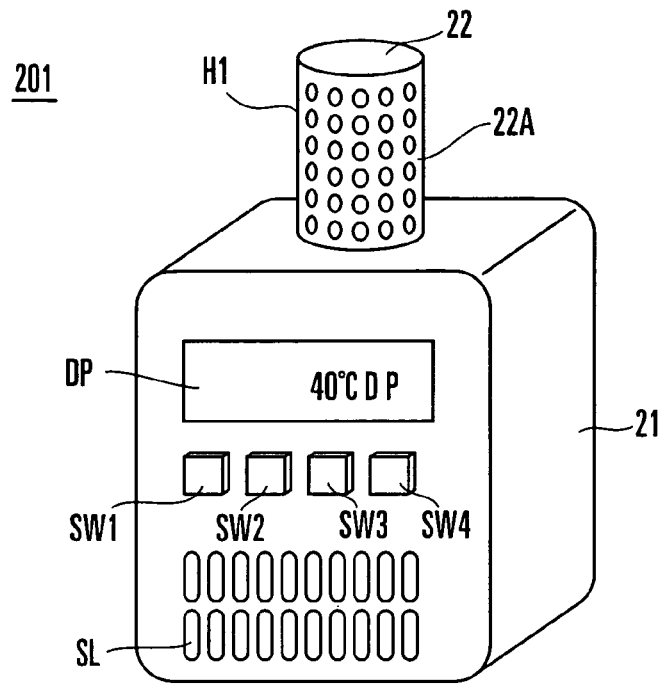
FIG. 4 is a perspective view showing the detailed arrangement of the mirror surface cooling dew point detector.
Figure 5:
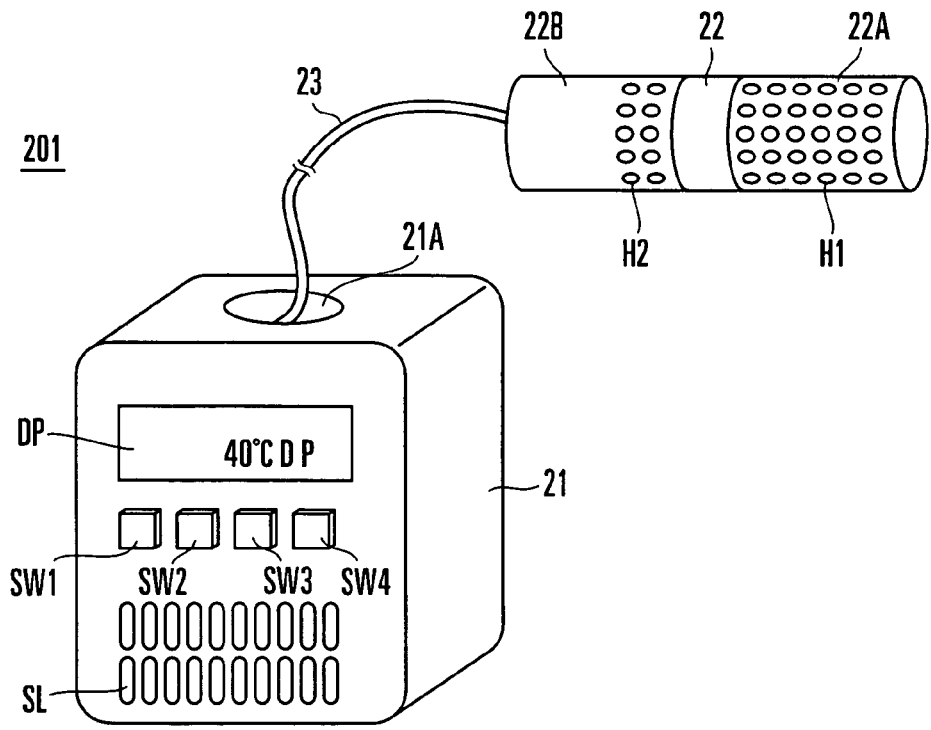
FIG. 5 is a view showing a state in which the sensor body is detached from the control box.

FIG. 4 shows the detailed arrangement of the mirror surface cooling dew point detector 201. In this example, the control unit 201B is accommodated in a control box (housing) 21. The sensor unit 201A is accommodated in a sensor body 22. The sensor body 22 can be detached from the control box 21. In the control box 21, a battery is used as the power supply to the control unit 201B. The sensor body 22 and control box 21 are connected by a cable 23, as shown in FIG. 5.

The cable 23 incorporates optical signal lines and electrical signal lines which connect the sensor unit 201A and control unit 201B. The cable 23 is long enough to detach the sensor body 22 from the control box 21 placed outside the measurement area and place only the control box 21 in the measurement area.

The sensor body 22 has covers 22A and 22B to cover the sensor unit 201A. The covers 22A and 22B have a number of vent holes H1 and H2. The mirror 10 is located in the cover 22A. When the sensor body 22 is mounted in the control box 21, the portion covered with the cover 22B is inserted in a recessed portion 21A of the control box 21. The portion (head of the sensor body 22) covered with the cover 22A projects from the upper surface of the control box 21. A number of vent holes H1 are provided in the cover 22A. When the sensor body 22 is mounted in the control box 21 (FIG. 4), or the sensor body 22 is detached from the control box 21 (FIG. 5), the mirror surface 10-1 of the mirror 10 located in the cover 22A is exposed to the outside air through the vent holes H1.

In this example, a battery is used as the power supply to the control unit 201B. Instead, a commercial AC power may be converted by an AC adapter into a DC current and used. A liquid crystal display unit DP serving as the dew point temperature display unit 12 is provided on the front surface of the control box 21. A power switch SW1, a display selector switch SW2 to select "dew point" or "air temperature", a heat/cool switch SW3 to forcibly heat or cool the mirror surface 10-1, and a backlight switch SW4 to turn on/off the backlight of the liquid crystal display unit DP are provided under the liquid crystal display unit DP. A number of radiating slits SL are provided in the control box 21.

In the mirror surface cooling dew point detector 201, the sensor body 22 mounted in the control box 21 can be placed on the measurement area. Alternatively, when the sensor body 22 is detached from the control box 21 placed outside the measurement area, only the sensor body 22 can be placed in the measurement area. In this case, the mirror surface 10-1 of the mirror 10 is exposed to the target measurement gas through the vent holes H1 f the cover 22A. The dew point temperature of the target measurement gas is detected by the above-described operation principle and displayed on the liquid crystal display unit DP.

Especially, in the mirror surface cooling dew point detector 201, the sensor body 22 can be detached from the control box 21 placed outside the measurement area, and only the sensor body 22 can be placed in the measurement area. Hence, even in a measurement area with a small space, the dew point temperature of the target measurement gas can be detected, resulting in high convenience. Since only two components, i.e., the sensor body 22 and control box 21 are included, and the sensor body 22 can integrally be mounted in the control box 21, the detector can more easily be carried.

When an ambient thermometer or pressure gauge is mounted in the sensor body 22, and a personal computer 24 is connected to the control box 21, as shown in FIG. 6, various kinds of arithmetic results such as the relative humidity, absolute water content, and saturated water vapor pressure can be displayed on the screen of the personal computer 24.

In the mirror surface cooling dew point detector 201 shown in FIG. 1, the sensor unit 201A uses the tube 17 which accommodates the light-emitting-side optical fiber 17-1 and light-receiving-side optical fiber 17-2. However, like a sensor unit 201A' shown in FIG. 7, a light-emitting diode 19 may be provided in place of the light-emitting-side optical fiber 17-1, and a photocoupler 20 may be provided in place of the light-receiving-side optical fiber 17-2.

Second Embodiment: Mirror surface Cooling Dew Point Detector (Regular-Reflected Light Detection Method)

Figure 8:
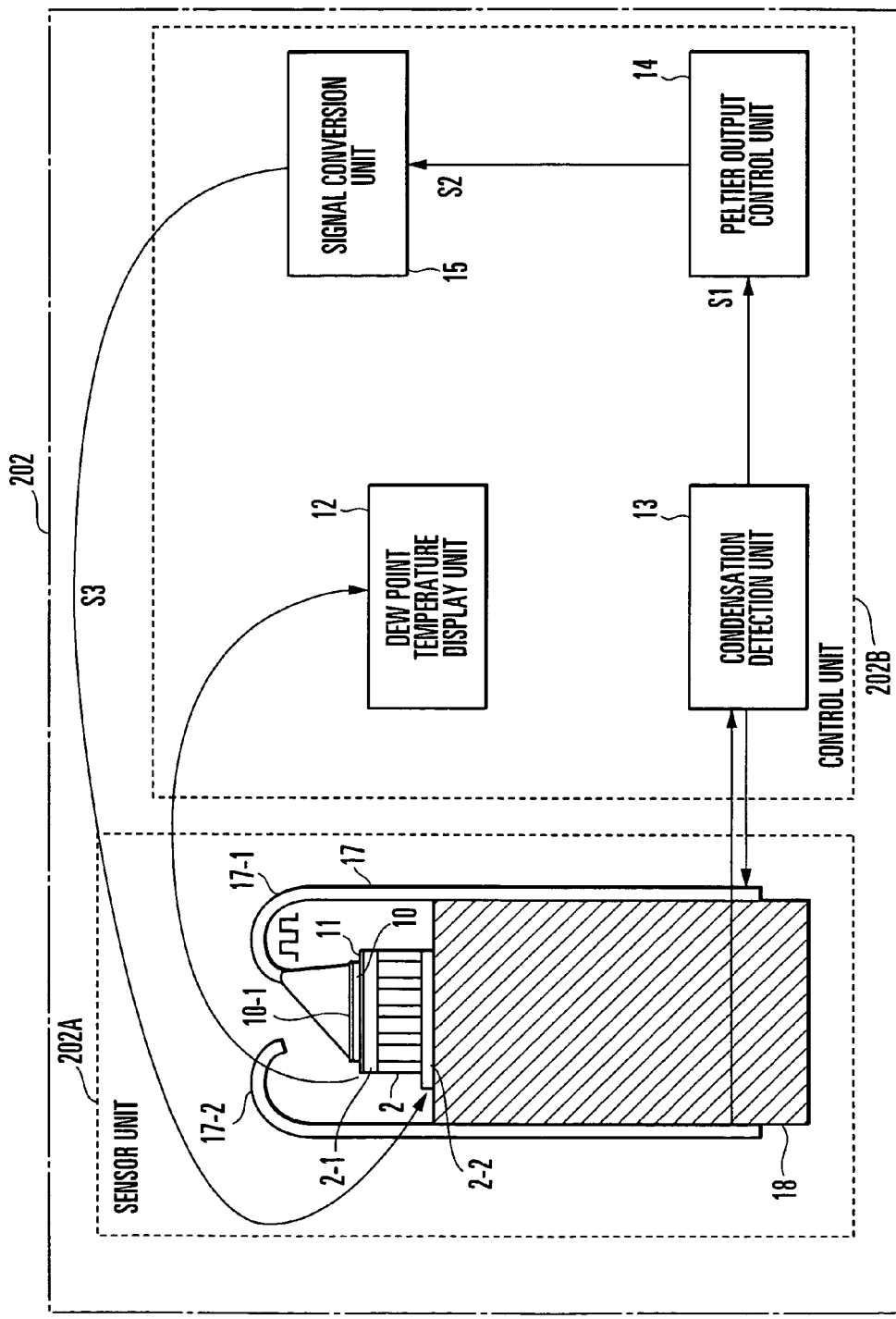
FIG. 8 is a schematic view showing another embodiment (second embodiment) of a mirror surface cooling dew point detector which uses a thermoelectric device according to the present invention.

FIG. 8 shows another embodiment (second embodiment) of a mirror surface cooling dew point detector which uses a thermoelectric device according to the present invention. In a mirror surface cooling dew point detector 202, a light-emitting-side optical fiber 17-1 and light-receiving-side optical fiber 17-2 are provided not in the same direction but on the left and right sides of a mirror 10 symmetrically. The distal end portions of the light-emitting-side optical fiber 17-1 and light-receiving-side optical fiber 17-2, which are curved into a J-shape, are directed to a mirror surface 10-1 of the mirror 10 and tilted at a predetermined tilt angle with respect to the mirror surface 10-1.

In the mirror surface cooling dew point detector 202, a sensor unit 202A is placed in the target measurement gas. A condensation detection unit 13 causes the optical fiber 17-1 to obliquely irradiate the mirror surface 10-1 of the mirror 10 with pulse light from the tip at a predetermined period. The mirror surface 10-1 is exposed to the target measurement gas. If no condensation occurs on the mirror surface 10-1, the pulse light emitted from the tip of the optical fiber 17-1 is almost wholly regularly reflected and received through the optical fiber 17-2. Hence, when no condensation occurs on the mirror surface 10-1, the intensity of the reflected pulse light received through the optical fiber 17-2 is high.

The condensation detection unit 13 obtains the difference between the upper limit value and lower limit value of the reflected pulse light received through the optical fiber 17-2 as the intensity of the reflected pulse light and sends a signal S1 corresponding to the reflected pulse light intensity to a Peltier output control unit 14. In this case, the reflected pulse light intensity is high and more than the threshold value, the Peltier output control unit 14 sends, to a signal conversion unit 15, a control signal S2 to increase the current to a thermoelectric cooling element 2. With this operation, a current S3 from the signal conversion unit 15 to the thermoelectric cooling element 2 increases, and the temperature of a cooled surface 2-1 of the thermoelectric cooling element 2 becomes low.

As the temperature of the cooled surface 2-1 of the thermoelectric cooling element 2, i.e., the temperature of the mirror 10 is decreased, vapor contained in the target measurement gas condenses on the mirror surface 10-1 of the mirror 10. The pulse light emitted from the tip of the optical fiber 17-1 is partially absorbed or diffused by the molecules of water. The intensity of the reflected pulse light (regular-reflected light) received from the mirror surface 10-1 through the optical fiber 17-2 decreases.

When the intensity of the reflected pulse light received through the optical fiber 17-2 is less than the threshold value, the Peltier output control unit 14 sends, to the signal conversion unit 15, the control signal S2 to decrease the current to the thermoelectric cooling element 2. With this operation, the decrease in temperature of the cooled surface 2-1 of the thermoelectric cooling element 2 is suppressed, and condensation is suppressed. When condensation is suppressed, the intensity of the reflected pulse light received through the optical fiber 17-2 becomes high. When the reflected pulse light intensity exceeds the threshold value, the Peltier output control unit 14 sends, to the signal conversion unit 15, the control signal S2 to increase the current to the thermoelectric cooling element 2. By repeating this operation, the temperature of the cooled surface 2-1 of the thermoelectric cooling element 2 is adjusted so that the intensity of reflected pulse light received through the optical fiber 17-2 almost equals the threshold value. The adjusted temperature, i.e., the temperature (dew point temperature) at which condensation which has occurred on the mirror surface 10-1 reaches the equilibrium state is displayed on a dew point temperature display unit 12 as the dew point temperature.

Even in the mirror surface cooling dew point detector 202, a temperature detection element 11 is provided between the mirror 10 and the cooled surface 2-1 of the thermoelectric cooling element 2. For this reason, the thermal resistance is low so that the temperature of the mirror 10 can be measured accurately at a high response. Hence, the dew point temperature measurement accuracy increases, and the response also increases. In addition, since any operation error by disturbance light can be prevented by the pulse modulation scheme, the chamber of the sensor unit 202A can be omitted.

Even in the mirror surface cooling dew point detector 202, a sensor body 22 is detachably mounted in a control box 21, as shown in FIG. 4 or 5, like the mirror surface cooling dew point detector 201 according to the first embodiment.

Figure 9:
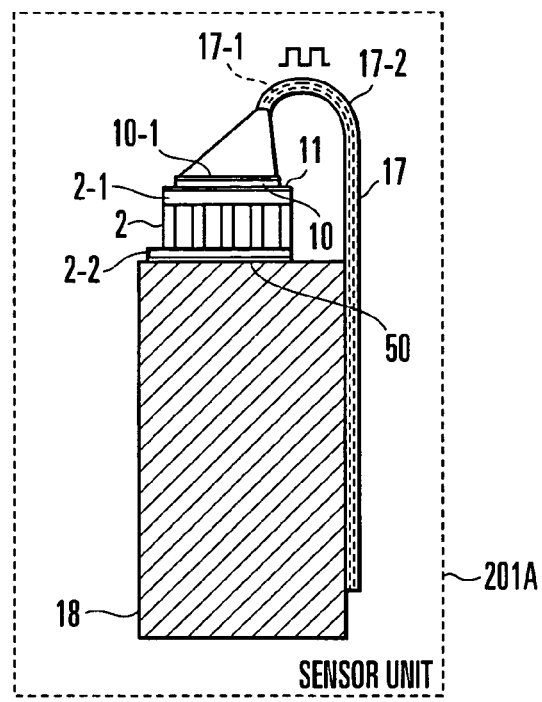
FIG. 9 is a view showing a modification of the sensor unit of the mirror surface cooling dew point detector according to the first embodiment in which a temperature detection element is also provided between the heat sink and the heated surface of the thermoelectric cooling element.
Figure 10:
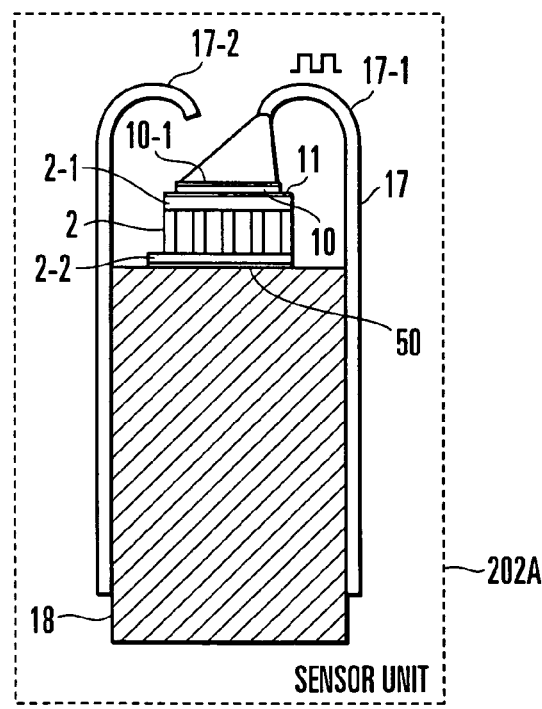
FIG. 10 is a view showing a modification of the sensor unit of the mirror surface cooling dew point detector according to the second embodiment in which a temperature detection element is also provided between the heat sink and the heated surface of the thermoelectric cooling element.

In the above-described first and second embodiments, the temperature detection element 11 is provided between the mirror 10 and the cooled surface 2-1 of the thermoelectric cooling element 2 to only detect the temperature of the mirror 10. As shown in FIG. 9 or 10, when a temperature detection element 50 may be provided between a heat sink 18 and a heated surface 2-2 of the thermoelectric cooling element 2. With this structure, the temperature of the heat sink 18 can be measured accurately at a high response. When the temperature of the heat sink 18 has reached a predetermined value, the current to the thermoelectric cooling element 2 is stopped or limited, thereby increasing the cooling efficiency of the mirror 10.

In the above-described first and second embodiments, condensation (moisture) on the mirror surface 10-1 is detected. With the same arrangement as described above, frost (moisture) on the mirror surface 10-1 can also be detected.

In the above-described first and second embodiments, the thermoelectric cooling element (Peltier element) 2 is used as the cooling means for cooling the mirror 10. However, a helium refrigerator may be used.

The sensor body 22 need not always be detachably mounted in the control box 21 and may permanently be mounted in the control box 21.

Figure 11A:
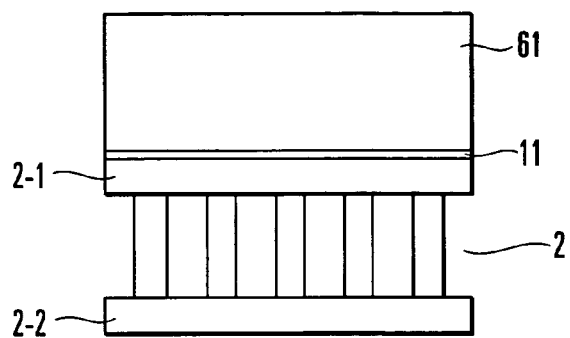
FIG. 11A is a view showing an application example of the present invention to a cooling device.
Figure 11B:
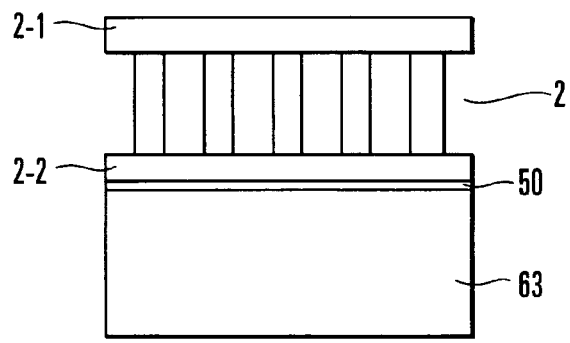
FIG. 11B is a view showing an application example of the present invention to a heating device.
Figure 11C:
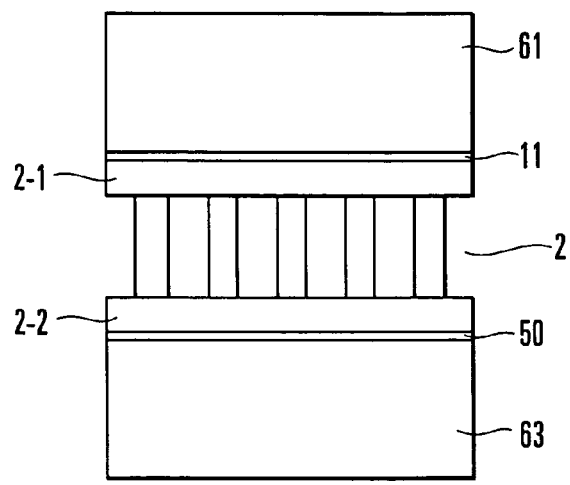
FIG. 11C is a view showing an application example of the present invention to a device which executes cooling and heating.
Figure 29:
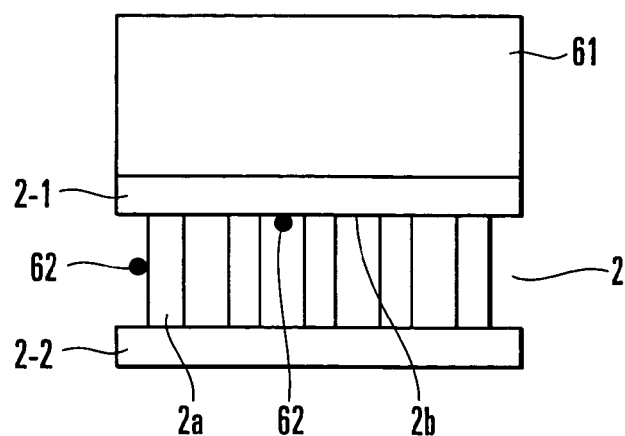
FIG. 29 is a view showing a temperature measurement structure in a conventional cooling device in which a CPU is attached to the cooled surface of a thermoelectric cooling element.
Figure 30:
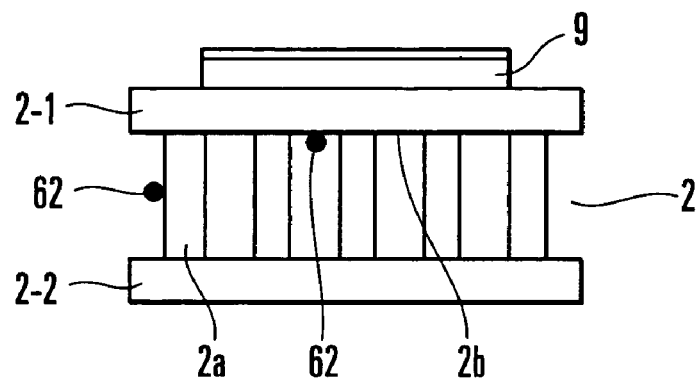
FIG. 30 is a view showing a structure to measure the temperature of the mirror surface in a mirror surface cooling dew point detector considered from the arrangement of the cooling device.
Figure 31:
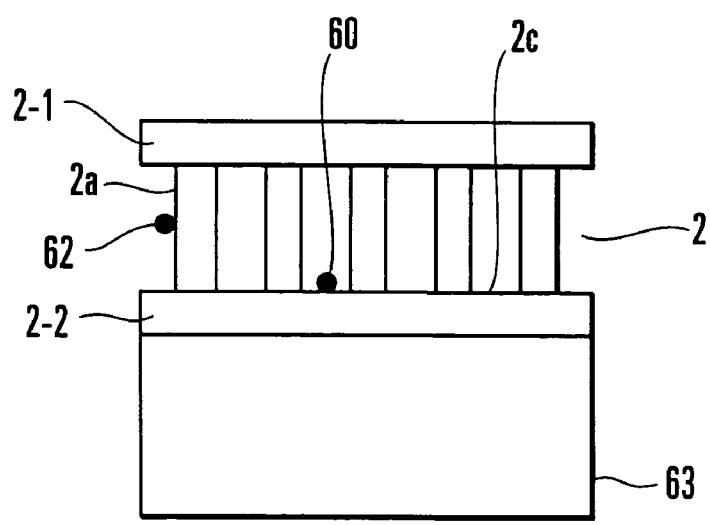
FIG. 31 is a view showing a temperature measurement structure in a conventional heating device in which a heated member is attached to the heated surface of a thermoelectric cooling element.

Mirror surface cooling dew point detectors have been described above. Even in the cooling device shown in FIG. 29, the temperature detection element 11 (FIG. 11A) may be provided between the CPU 61 and the cooled surface 2-1 of the thermoelectric cooling element 2. Even in the heating device shown in FIG. 31, the temperature detection element 50 (FIG. 11B) may be provided between the heated member 63 and the heated surface 2-2 of the thermoelectric heating element 2. As shown in FIG. 11C, the temperature detection element 11 may be provided between the CPU 61 and the cooled surface 2-1 of the thermoelectric cooling element 2, and simultaneously, the temperature detection element 50 may be provided between the heated member (heat radiating member) 30 and the heated surface 2-2 of the thermoelectric heating element 2.

The temperature detection element 11 or 50 need not always be provided on the entire surface between the mirror 10 and the cooled surface 2-1 of the thermoelectric cooling element 2 or between the heat sink 18 and the heated surface 2-2 of the thermoelectric cooling element 2. Instead, a band-shaped pattern may be formed.

Figure 28:
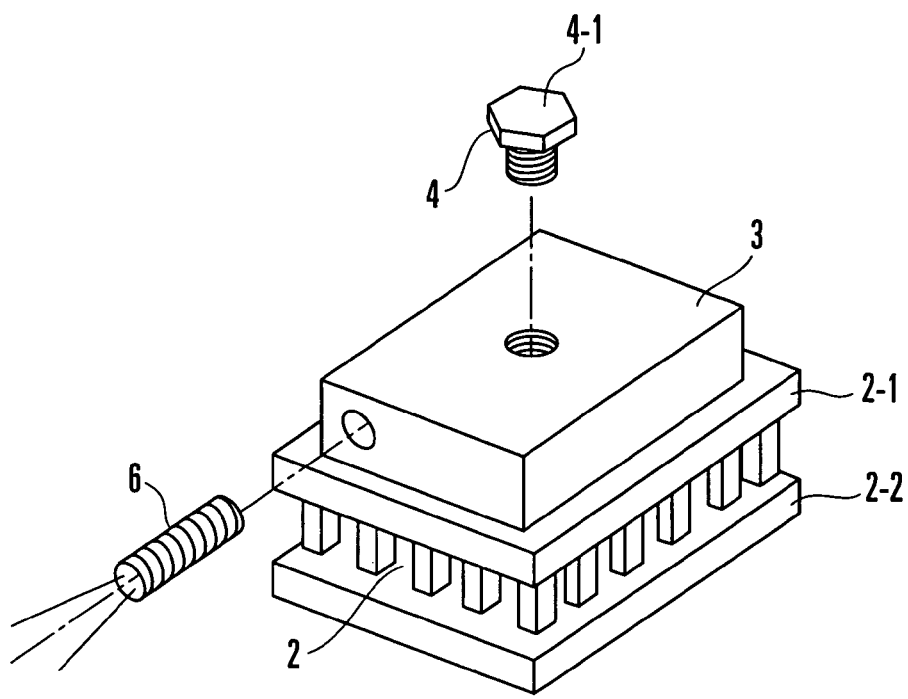
FIG. 28 is a perspective view showing the attachment structure of a mirror or temperature detection element in the conventional mirror surface cooling dew point detector.

In the arrangement shown in FIG. 28, the temperature detection element 6 may be omitted, and instead, the temperature detection element 11 may be provided between the copper block 3 and the cooled surface 2-1 of the thermoelectric cooling element 2.

First Application Example of Pulse Modulation Scheme: Weather Detector (Scattered Light Detection Method)

Figure 12:
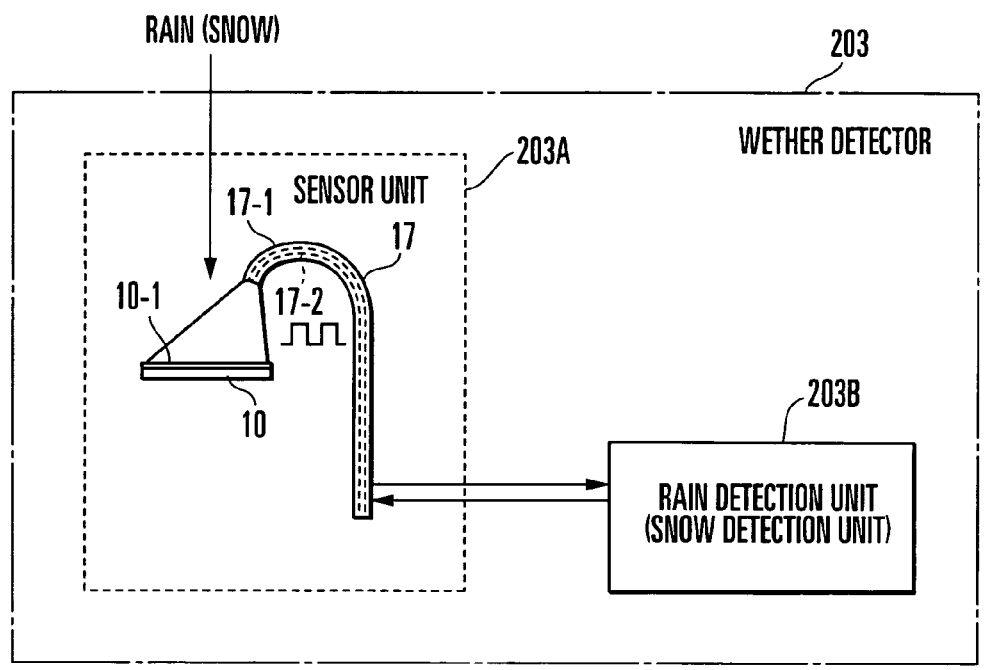
FIG. 12 is a schematic view showing the first example of a weather detector using a pulse modulation scheme.

FIG. 12 shows the first example of a weather detector using the above-described pulse modulation scheme. A weather detector 203 has a sensor unit 203A and rain detection unit 203B. In the sensor unit 203A, only the mirror 10 is provided. The tube 17 with the upper end portion curved into a J-shape is provided.

In the weather detector 203, the rain detection unit 203B causes the optical fiber 17-1 to obliquely irradiate the mirror surface 10-1 of the mirror 10 with pulse light from the tip at a predetermined period. The rain detection unit 203B also obtains the difference between the upper limit value and lower limit value of reflected pulse light (scattered light) received through the optical fiber 17-2 as the intensity of the reflected pulse light and compares the reflected pulse light intensity with a predetermined threshold value. If the reflected pulse light intensity exceeds the threshold value, it is determined that it begins to rain (rain sticks to the mirror surface 10-1).

Second Application Example of Pulse Modulation Scheme: Weather Detector (Regular-Reflected Light Detection Method)

Figure 13:
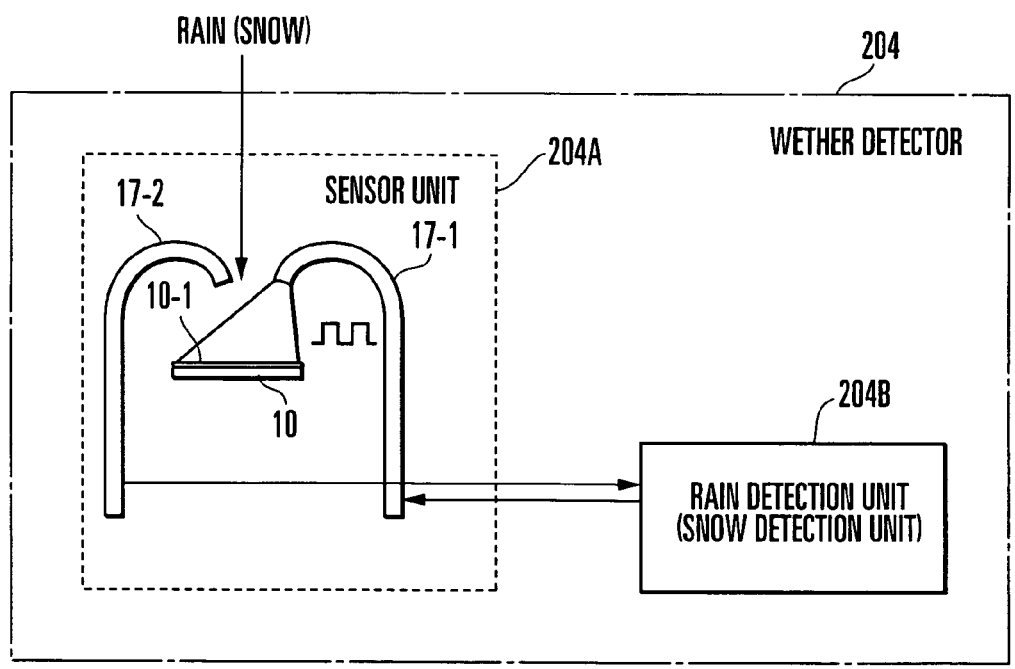
FIG. 13 is a schematic view showing the second example of a weather detector using the pulse modulation scheme.

FIG. 13 shows the second example of a weather detector using the above-described pulse modulation scheme. A weather detector 204 has a sensor unit 204A and rain detection unit 204B. In the sensor unit 204A, only the mirror 10 is provided. The light-emitting-side optical fiber 17-1 and light-receiving-side optical fiber 17-2 with the upper end portions curved into a J-shape are provided on the left and right sides of the mirror 10 symmetrically.

In the weather detector 204, the rain detection unit 204B causes the optical fiber 17-1 to obliquely irradiate the mirror surface 10-1 of the mirror 10 with pulse light from the tip at a predetermined period. The rain detection unit 204B also obtains the difference between the upper limit value and lower limit value of reflected pulse light (regular-reflected light) received through the optical fiber 17-2 as the intensity of the reflected pulse light and compares the reflected pulse light intensity with a predetermined threshold value. If the reflected pulse light intensity is less than the threshold value, it is determined that it begins to rain (rain sticks to the mirror surface 10-1).

In the above-described first and second examples of the weather detector, rain sticking to the mirror surface 10-1 is detected. With the same arrangement as described above, snow sticking to the mirror surface 10-1 can also be detected. With the same arrangement as described above, not only rain or snow but also dust or the like can also be detected.

Third Embodiment: S-Type

Figure 14:
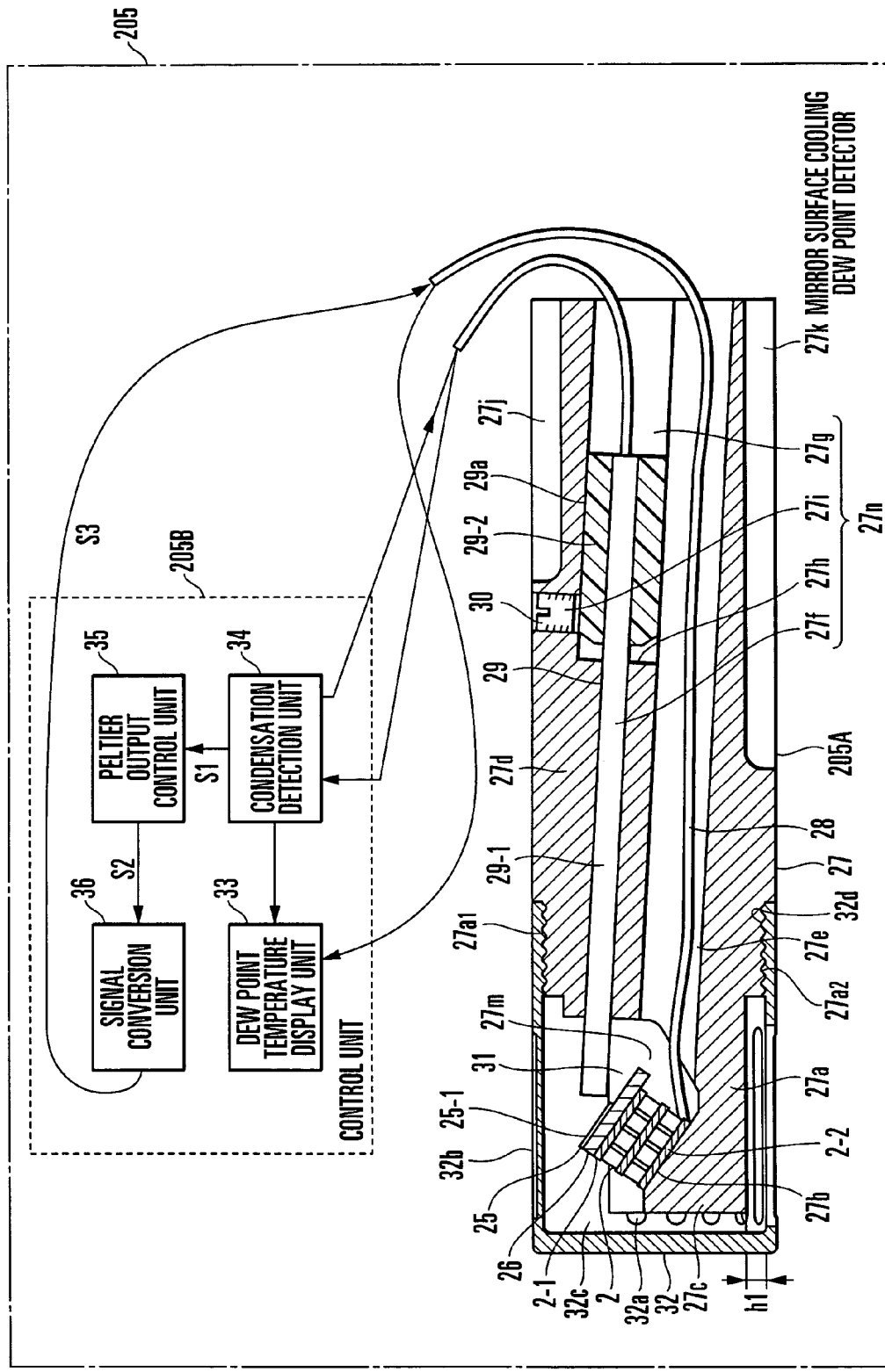
FIG. 14 is a schematic view showing still another embodiment (third embodiment: using an S-type mirror surface cooling sensor) of a mirror surface cooling dew point detector which uses a thermoelectric device according to the present invention.

FIG. 14 shows still another embodiment (third embodiment) of a mirror surface cooling dew point detector which uses a thermoelectric device according to the present invention. A mirror surface cooling dew point detector 205 has a sensor unit (mirror surface cooling sensor) 205A and control unit 205B. In the present invention, the mirror surface cooling sensor 205A shown in FIG. 14 will be referred to as an S-type mirror surface cooling sensor.

In the S-type mirror surface cooling sensor 205A, a mirror 25 is attached to a cooled surface 2-1 of a thermoelectric cooling element (Peltier element) 2. The mirror 25 is formed from, e.g., a silicon chip whose surface 25-1 is a mirror surface. A temperature detection element 26 made of, e.g., platinum is provided between the mirror 25 and the cooled surface 2-1 of the thermoelectric cooling element 2. The thermoelectric cooling element 2 having a heated surface 2-2 as the bottom surface is attached to an inclined surface 27b at a distal end portion 27a of a heat conductor 27 made of copper. The inclined surface 27b has a tilt angle of 30° to 45° with respect to the central axis of the heat conductor 27. Hence, the mirror surface 25-1 of the mirror 25 attached to the cooled surface 2-1 of the thermoelectric cooling element 2 is also tilted at 30° to 45° with respect to the central axis of the heat conductor 27.

Figure 15:
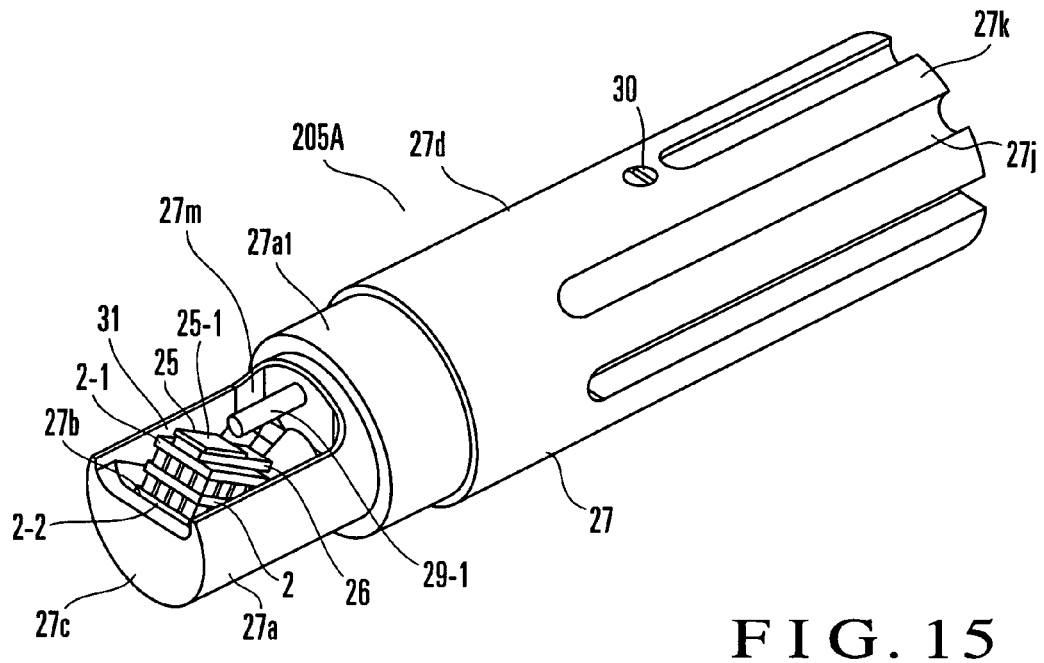
FIG. 15 is a perspective view showing the attached state of the thermoelectric cooling element at the distal end portion of a heat conductor.
Figure 16A:
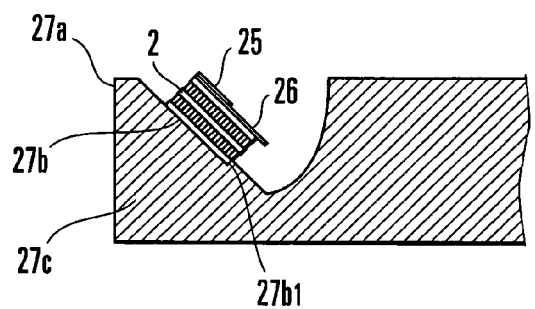
FIG. 16A is a schematic view for explaining the longitudinal-direction aligned state of the thermoelectric cooling element on the inclined surface provided at the distal end portion of the heat conductor.
Figure 16B:
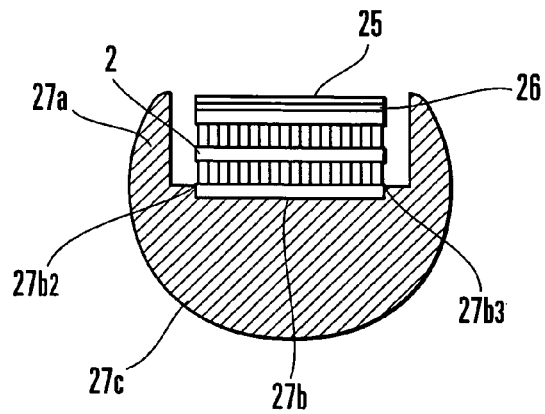
FIG. 16B is a schematic view for explaining the lateral-direction aligned state of the thermoelectric cooling element on the inclined surface provided at the distal end portion of the heat conductor.

The inclined surface 27b at the distal end portion 27a of the heat conductor 27 is formed by cutting. That is, a chamber 27m to accommodate the thermoelectric cooling element 2 at the distal end portion 27a of the heat conductor 27 is formed by cutting. FIG. 15 shows the attached state of the thermoelectric cooling element 2 at the distal end portion 27a of the heat conductor 27. The heat conductor 27 has a cylindrical shape. The chamber 27m is formed by hollowing the distal end portion 27a by cutting. The thermoelectric cooling element 2 is fixed to the inclined surface 27b of the chamber 27m by solder or the like. The longitudinal alignment of the thermoelectric cooling element 2 on the inclined surface 27b is done by a step 27b1 provided midway on the inclined surface 27b, as schematically shown in FIG. 16A. The lateral alignment of the thermoelectric cooling element 2 on the inclined surface 27b is done by steps 27b2 and 27b3 provided on left and right sides on the inclined surface 27b, as schematically shown in FIG. 16B.

Figure 17:
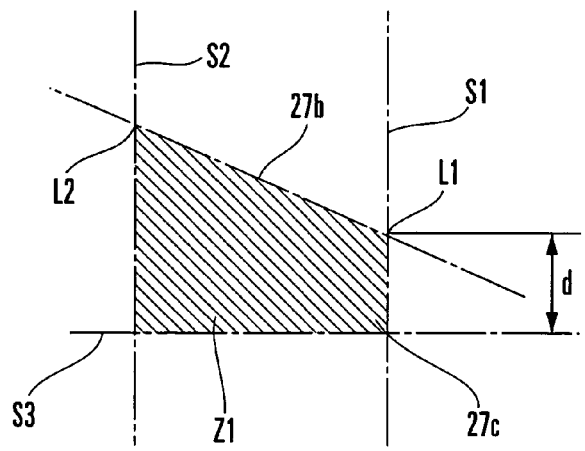
FIG. 17 is a view for explaining a thick portion provided under the inclined surface at the distal end portion of the heat conductor.

At the distal end portion 27a of the heat conductor 27, a thick portion 27c is present under the inclined surface 27b. More specifically, as shown in FIG. 17, the thick portion 27c in which the substance contained in the heat conductor 27 is present is arranged in a space Z1 surrounded by a first vertical surface S1 which crosses a leading edge L1 of the inclined surface 27b, a second vertical surface S2 which crosses a trailing edge L2 of the inclined surface 27b, a horizontal surface S3 which is spaced apart from the leading edge L1 of the inclined surface 27b by at least a predetermined distance d and crosses the vertical surfaces S1 and S2, and the inclined surface 27b.

A through hole 27e through which a lead wire 28 to the thermoelectric cooling element 2 passes is provided in a trunk 27d connected to the distal end portion 27a of the heat conductor 27. A holding portion 27n which holds an optical fiber 29 is formed integrally with the trunk 27d. In this embodiment, an optical fiber which has a small-diameter fiber portion 29-1 and a large-diameter fiber portion 29-2 connected to the small-diameter fiber portion 29-1 and whose light-projecting axis and light-receiving axis are parallel is used as the optical fiber 29. The structure of the optical fiber 29 will be described later. The lead wire 28 to the thermoelectric cooling element 2 includes a lead wire for current supply to the thermoelectric cooling element 2 and a lead wire for signal derivation from the temperature detection element 26.

In the heat conductor 27, the holding portion 27n for the optical fiber 29 comprises a through hole 27f, communicating hole 27g, wall (boundary between the through hole 27f and the communicating hole 27g) 27h, and threaded hole 27i. The small-diameter fiber portion 29-1 is inserted in the through hole 27f. The communicating hole 27g communicates with the through hole 27f. The large-diameter fiber portion 29-2 is located in the communicating hole 27g. The wall 27h is located between the through hole 27f and the communicating hole 27g to regulate the sliding position of the large-diameter fiber portion 29-2 in the communicating hole 27g such that the tip of the small-diameter fiber portion 29-1 does not abut against the mirror surface 25-1 of the mirror 25. A screw 30 to fix the sliding position of the large-diameter fiber portion 29-2 in the communicating hole 27g to an arbitrary position is attached to the threaded hole 27i.

In this embodiment, the small-diameter fiber portion 29-1 of the optical fiber 29 is inserted from the rear side in the communicating hole 27g. The inserted small-diameter fiber portion 29-1 is inserted in the through hole 27f, thereby locating the large-diameter fiber portion 29-2 in the communicating hole 27g. The sliding position of the large-diameter fiber portion 29-2 in the communicating hole 27g is regulated by the wall 27h as a boundary between the through hole 27f and the communicating hole 27g. At the regulated position, a small gap is formed between the tip of the small-diameter fiber portion 29-1 and the mirror surface 25-1 of the mirror 25. Hence, in this embodiment, even when the large-diameter fiber portion 29-1 of the optical fiber 29 is fully slidably moved in the communicating hole 27g, the tip of the small-diameter fiber portion 29-1 can be prevented from abutting against the mirror surface 25-1 of the mirror 25.

The distance between the tip of the small-diameter fiber portion 29-1 and the mirror surface 25-1 of the mirror 25 can be adjusted by slidably moving the optical fiber 29 in the longitudinal direction. In this embodiment, after the distance between the tip of the small-diameter fiber portion 29-1 and the mirror surface 25-1 of the mirror 25 is adjusted, the screw 30 set in the threaded hole 27i from the outside of the heat conductor 27 is tightened, thereby fixing the sliding position of the large-diameter fiber portion 29-2 in the communicating hole 27g The through hole 27e in which the lead wire 28 to the thermoelectric cooling element 2 is inserted communicates with the communicating hole 27g included in the holding portion 27n for the optical fiber 29 behind the trunk 27d. For this reason, the sectional shape of the communicating hole 27g is not completely circular, and its lower end is partially cut. Even when the lower end is partially cut, the sectional shape of the communicating hole 27g is an arc equal to or larger than a semicircle. Hence, the large-diameter fiber portion 29-2 of the optical fiber 29 can slidably be moved without any problem.

In this embodiment, the central axes of the through hole 27e and the communicating hole 27g of the holding portion 27n for the optical fiber 29 are slightly tilted with respect to the central axis of the heat conductor 27. The optical fiber 29 is attached while tilting its optical axis with respect to the heat conductor 27 so that the large-diameter fiber portion 29-2 is located near the central portion of the heat conductor 27, and the small-diameter fiber portion 29-1 is located near the outer periphery of the heat conductor 27.

Semicircular recessed portions 27j are formed in the rear outer surface of the trunk 27d of the heat conductor 27. A three-dimensional pattern formed by the recessed portions 27j serves as a radiating portion 27k of the heat conductor 27. That is, in this embodiment, not only the holding portion 27n for the optical fiber 29 but also the radiating portion 27k is formed integrally with the heat conductor 27.

A cylindrical mirror cover (cap) 32 having a closed end is attached to the distal end portion 27a of the heat conductor 27. More specifically, in this embodiment, a detection unit 31 having the thermoelectric cooling element 2 as the main constituent element is provided at the distal end portion 27a of the heat conductor 27. The detection unit 31 is covered with the mirror cover 32. In this state, a small gap h1 (FIG. 14) is provided between the inner surface of the mirror cover 32 and the outer surface of the distal end portion 27a of the heat conductor 27.

Figure 18:
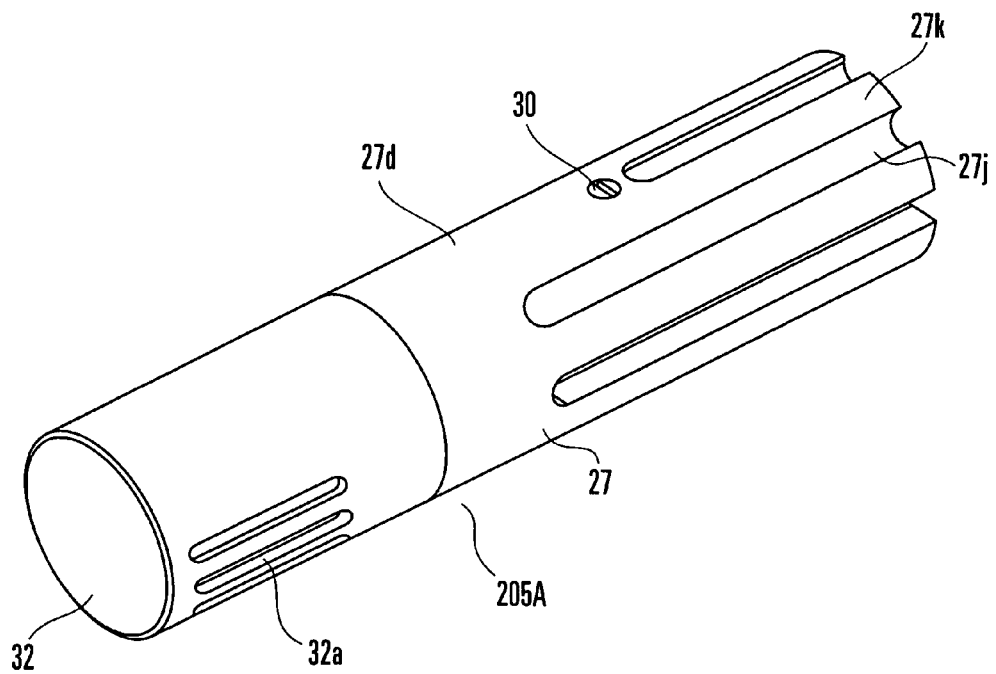
FIG. 18 is a perspective view showing the S-type mirror surface cooling sensor having a mirror cover attached to the detection unit.
Figure 19:
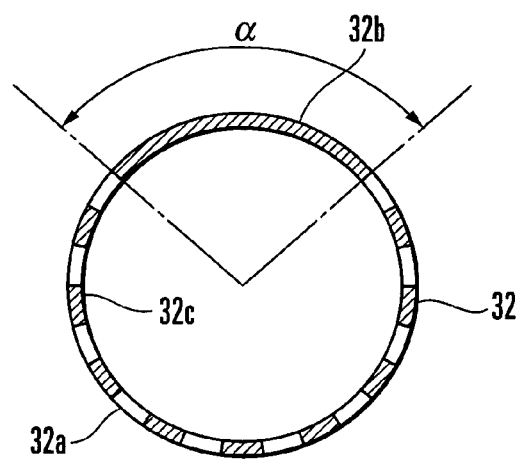
FIG. 19 is a sectional view showing a predetermined range α in the mirror cover.

The mirror cover 32 is made of a material having a high heat conduction. Vent holes 32a are formed in the side surface of the mirror cover 32 (FIG. 18). The vent holes 32a in the mirror cover 32 are provided in the range except a predetermined angular range α (FIG. 19) opposing the mirror surface 25-1 of the mirror 25 attached to the cooled surface 2-1 of the thermoelectric cooling element 2 when the mirror cover 32 is attached to the distal end portion 27a of the heat conductor 27. That is, no vent holes (ventilating portions) 32a are formed in the predetermined angular range α of the mirror cover 32. This portion serves as a light-shielding portion 32b (wall having no vent holes 32a) which shields direct light (external disturbance light) from the outside to the mirror surface 25-1. In this embodiment, an optical absorption treatment (e.g., black coating) is executed for an inner surface 32c of the mirror cover 32 to absorb light.

The mirror cover 32 is attached to the detection unit 31 by threadably engaging the mirror cover 32 on a proximal portion 27a1 of the distal end portion 27a of the heat conductor 27. More specifically, a screw portion 32d is formed at the lower end portion of the inner surface 32c of the mirror cover 32. A screw portion 27a2 is formed at the proximal portion 27a1 of the distal end portion 27a of the heat conductor 27. The mirror cover 32 is attached to the distal end portion 27a of the heat conductor 27 by threadably engaging the screw portion 32d on the screw portion 27a2. With this thread engaging structure, when the mirror cover 32 is fully tightened, the light-shielding portion 32b of the mirror cover 32 always opposes the mirror surface 25-1. In this example, the thread engaging structure of the screw thread and thread groove is used as the means for regulating the attachment position of the mirror cover 32. For example, a step portion to regulate the rotational angular position of the mirror cover 32 may be provided, and the mirror cover 32 may be pressed into it.

The mirror cover 32 is made of a material having a high heat conduction due to the following reasons. The detection unit 31 is placed in the target measurement gas. When the target measurement gas changes from a low temperature and low humidity to a high temperature and high humidity, condensation occurs on the mirror cover 32 if it is poor in heat conduction, and the water content cannot accurately be measured. Additionally, in measuring the target measurement gas at a high humidity, the entire structure must be heated to prevent condensation on the mirror cover 32. To uniformly heat the structure, the material preferably has a high heat conduction.

As described above, an optical fiber which has the small-diameter fiber portion 29-1 and the large-diameter fiber portion 29-2 connected to the small-diameter fiber portion 29-1 and whose light-projecting axis and light-receiving axis are parallel is used as the optical fiber 29. In this embodiment, by setting the light-projecting axis and light-receiving axis parallel, the light irradiation direction (light-projecting-side optical axis) from the tip of the small-diameter fiber portion 29-1 and the light-receiving direction (light-receiving-side optical axis) are made parallel. In addition, the light-projecting-side optical axis and light-receiving-side optical axis are adjacent at the same tilt angle. The small-diameter fiber portion 29-1 can have various forms as shown in FIGS. 2A to 2E.

The rear portion of the small-diameter fiber portion 29-1 is covered with a cylindrical sleeve 29a so that the large-diameter fiber portion 29-2 is formed. In this embodiment, the screw 30 is tightened from the outside of the heat conductor 27, thereby pressing the tip of the screw 30 against the large-diameter fiber portion 29-2. This pressing force is received by the sleeve 29a. Hence, any adverse effect on the optical fiber accommodated in the small-diameter fiber portion 29-1 can be prevented.

The control unit 205B comprises a dew point temperature display unit 33, condensation detection unit 34, Peltier output control unit 35, and signal conversion unit 36. The temperature of the mirror 25 detected by the temperature detection element 26 is displayed on the dew point temperature display unit 33. The condensation detection unit 34 causes the optical fiber 29 to obliquely irradiate the mirror surface 25-1 of the mirror 25 with pulse light from the tip at a predetermined period. In addition, the condensation detection unit 34 obtains the difference between the upper limit value and lower limit value of reflected pulse light (scattered light) received through the optical fiber 29 as the intensity of the reflected pulse light and sends a signal S1 corresponding to the reflected pulse light intensity to the Peltier output control unit 35. Upon receiving the signal S1 from the condensation detection unit 34, the Peltier output control unit 35 compares the reflected pulse light intensity with a predetermined threshold value. If the reflected pulse light intensity is less than the threshold value, the Peltier output control unit 35 outputs, to the signal conversion unit 36, a control signal S2 to increase the current to the thermoelectric cooling element 2 in accordance with the value of the signal S1. If the reflected pulse light intensity exceeds the threshold value, the Peltier output control unit 35 outputs, to the signal conversion unit 36, the control signal S2 to decrease the current to the thermoelectric cooling element 2 in accordance with the value of the signal S1. The signal conversion unit 36 supplies, to the thermoelectric cooling element 2, a current S3 indicated by the control signal S2 from the Peltier output control unit 35.

Figure 20:
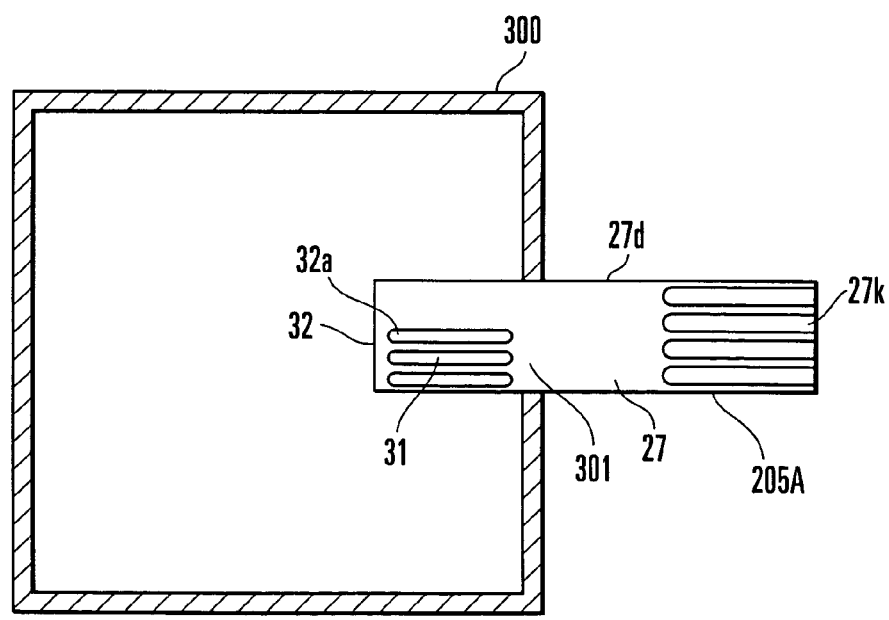
FIG. 20 is a view showing the attached state of the S-type mirror surface cooling sensor to a duct.

When the dew point of moisture in the target measurement gas flowing through, e.g., a duct is to be detected by the mirror surface cooling dew point detector 205, the mirror surface cooling sensor 205A is attached to a duct 300, as shown in FIG. 20. More specifically, the detection unit 31 covered with the mirror cover 32 is inserted in an attachment hole 301 formed in the side surface of the duct 300. Although FIG. 20 does not illustrate the attachment structure of the mirror surface cooling sensor 205A to the duct 300, it can be attached to the duct 300 by various methods by using, e.g., a bracket.

When the mirror surface cooling sensor 205A is attached to the duct 300, the detection unit 31 is located in the duct 300, and the radiating portion 27k is located outside the duct 300. The target measurement gas flowing through the duct 300 enters the detection unit 31 through the vent holes 32a of the mirror cover 32. The mirror surface 25-1 of the mirror 25 is exposed to the target measurement gas. When the sensor is exposed to the target measurement gas, the thermoelectric cooling element 2 and mirror 25 of the detection unit 31 are protected by the mirror cover 32. In this case, since the small gap h1 is formed between the inner surface of the mirror cover 32 and the outer surface of the distal end portion 27a of the heat conductor 27, the target measurement gas enters the gap h1 and satisfactorily circulates at the detection unit 31.

When the mirror surface cooling sensor 205A is attached to the duct 300, the condensation detection unit 34 causes the optical fiber 29 to irradiate the mirror surface 25-1 of the mirror 25 with pulse light from the tip at a predetermined period (FIG. 3A). The mirror surface 25-1 is exposed to the target measurement gas. If no condensation occurs on the mirror surface 25-1, the pulse light emitted from the tip of the optical fiber 29 is almost wholly regularly reflected. The amount of reflected pulse light (scattered light) received from the mirror surface 25-1 through the optical fiber 29 is very small. Hence, when no condensation occurs on the mirror surface 25-1, the intensity of reflected pulse light received through the optical fiber 29 is low.

The condensation detection unit 34 obtains the difference between the upper limit value and lower limit value of the reflected pulse light received through the optical fiber 29 as the intensity of the reflected pulse light and sends the signal S1 corresponding to the reflected pulse light intensity to the Peltier output control unit 35. In this case, the reflected pulse light intensity is almost zero and less than the predetermined threshold value. For this reason, the Peltier output control unit 35 sends, to the signal conversion unit 36, the control signal S2 to increase the current to the thermoelectric cooling element 2. With this operation, the current S3 from the signal conversion unit 36 to the thermoelectric cooling element 2 increases, and the temperature of the cooled surface 2-1 of the thermoelectric cooling element 2 becomes low.

As the temperature of the cooled surface 2-1 of the thermoelectric cooling element 2, i.e., the temperature of the mirror 25 is decreased, vapor contained in the target measurement gas condenses on the mirror surface 25-1 of the mirror 25. The pulse light emitted from the tip of the optical fiber 29 is partially absorbed or diffused by the molecules of water. The intensity of the reflected pulse light (scattered light) received from the mirror surface 25-1 through the optical fiber 29 increases.

The condensation detection unit 34 obtains the difference between the upper limit value and lower limit value of each pulse of the received reflected pulse light as the intensity of the reflected pulse light. More specifically, as shown in FIG. 3B, a difference ΔL between an upper limit value Lmax and lower limit value Lmin of one pulse of the reflected pulse light is obtained as the intensity of the reflected pulse light. By the processing by the condensation detection unit 34, disturbance light ΔX contained in the reflected pulse light is removed. Hence, any operation error by disturbance light can be prevented. With this processing, the chamber to shield light from the mirror surface cooling sensor 205A can be omitted from the mirror surface cooling dew point detector 205.

If the intensity of the reflected pulse light received through the optical fiber 29 exceeds the threshold value, the Peltier output control unit 35 sends, to the signal conversion unit 36, the control signal S2 to decrease the current to the thermoelectric cooling element 2. With this operation, the decrease in temperature of the cooled surface 2-1 of the thermoelectric cooling element 2 is suppressed, and condensation is suppressed. When condensation is suppressed, the intensity of the reflected pulse light received through the optical fiber 29 becomes low. When the reflected pulse light intensity is less than the threshold value, the Peltier output control unit 35 sends, to the signal conversion unit 36, the control signal S2 to increase the current to the thermoelectric cooling element 2. By repeating this operation, the temperature of the cooled surface 2-1 of the thermoelectric cooling element 2 is adjusted so that the intensity of reflected pulse light received through the optical fiber 29 almost equals the threshold value. The adjusted temperature, i.e., the temperature (dew point temperature) at which condensation which has occurred on the mirror surface 25-1 reaches the equilibrium state is displayed on the dew point temperature display unit 33 as the dew point temperature.

Even in the mirror surface cooling dew point detector 205, the temperature detection element 26 is provided between the mirror 25 and the cooled surface 2-1 of the thermoelectric cooling element 2. For this reason, the thermal resistance is low so that the temperature of the mirror 25 can be measured accurately at a high response. Hence, the dew point temperature measurement accuracy can be increased, and the response can also be increased. In this embodiment, condensation (moisture) on the mirror surface 25-1 is detected. With the same arrangement as described above, frost (moisture) on the mirror surface 25-1 can also be detected.

In the dew point detection operation, in the mirror surface cooling sensor 205A, when the temperature of the cooled surface 2-1 of the thermoelectric cooling element 2 decreases, the temperature of the heated surface 2-2 rises. Heat generated by the rising temperature of the heated surface 2-2 is transmitted from the inclined surface 27b at the distal end portion 27a of the heat conductor 27 through the trunk 27d and dissipated from the radiating portion 27k located outside the duct 300.

In this embodiment, the predetermined angular range α of the mirror cover 32 attached to the distal end portion 27a of the heat conductor 27, i.e., the light-shielding portion (wall) 32b having no vent holes 32a opposes the mirror surface 25-1. For this reason, neither external disturbance light nor dust enters the detection unit 31 from the light-shielding portion 32b. The target measurement gas does not blow down from the position opposing the mirror surface 25-1. Since the optical absorption treatment is executed for the inner surface 32c of the mirror cover 32, internal disturbance light is reduced. Hence, in detecting the dew point temperature, the reliability of detection accuracy can be increased. In this example, the optical absorption treatment is executed for the inner surface 32c of the mirror cover 32. However, the optical absorption treatment on the inner surface 32c of the mirror cover 32 may be omitted.

In place of the mirror cover 32, a cover 32' (FIG. 21) made of a sintered metal may be provided. The sintered metal has the light-shielding effect and ventilation property. That is, the sintered metal has an infinite number of pores which are so fine that no light can pass through. The fine pores serve as the ventilating portions to the inside, and the remaining part serves as the light-shielding portion to shield external light. With this structure, direct light (external disturbance light) from the outside to the mirror surface 25-1 can be shielded while flowing the target measurement gas into the cover 32'. An inner surface 32'c of the cover 32' may be subjected to the optical absorption treatment, like the mirror cover 32. The sintered metal is a member which uses metal powder as a material and is generally used, and a detailed description thereof will be omitted.

The cover 32' made of the sintered metal may be covered with a protective cover 42 (FIG. 22) having vent holes 42' formed in the entire side surface. When the cover 32' is covered with the protective cover 42, the cover 32' can be protected from collision of foreign substances contained in the target measurement gas. In this case, the cover 32' functions as a kind of filter. Vent holes 42a to the protective cover 42 may be formed outside a portion corresponding to the predetermined angular range α shown in FIG. 19.

In this embodiment, the heat conductor 27 has a large volume because the holding portion 27n for the optical fiber 29 and the radiating portion 27k are integrated. In addition, since the heat conductor 27 has no joints to the holding portion and radiating portion, no heat reservoir is generated at such joints. With this structure, a high heat exhausting effect can be obtained, and more heat can be moved to the cool side and dissipated without using any heat pipe. Furthermore, the holding portion and radiating portion are not necessary as separate components. For this reason, the number of components can be decreased. The cost can also be reduced because no heat pipe is used.

The heat pipe is formed by vacuum-sealing a small amount of liquid (hydraulic fluid) in a closed vessel and has a capillary structure on the inner wall. When part of the heat pipe is heated, the hydraulic fluid evaporates at the heated portion (absorption of latent heat of vaporization). The vapor moves to a cool portion and condenses at the cool portion (discharge of latent heat of vaporization). The condensed liquid circulates to the heated portion by the capillary phenomenon. The series of phase changes continuously occur so that the heat quickly moves from the heated portion to the cool portion.

In this embodiment, the optical fiber 29 is attached not parallelly but slightly obliquely with respect to the central axis of the heat conductor 27. The large-diameter fiber portion 29-2 is located near the central portion of the heat conductor 27, and the small-diameter fiber portion 29-1 is located near the outer periphery of the heat conductor 27. Hence, the outer peripheral portion of the heat conductor 27 can be made thick. With this structure, the outer diameter of the heat conductor 27 decreases, and size reduction can be implemented.

In this embodiment, assembly, detachment, or position adjustment of the optical fiber 29 is easy. More specifically, to assemble the optical fiber 29, the small-diameter fiber portion 29-1 is inserted from the rear side of the communicating hole 27g. The inserted small-diameter fiber portion 29-1 is inserted in the through hole 27f to locate the large-diameter fiber portion 29-2 in the communicating hole 27g. The screw 30 set in the threaded hole 27i is tightened from the outside of the heat conductor 27. To adjust the position of the optical fiber 29, i.e., adjust the distance between the tip of the small-diameter fiber portion 29-1 and the mirror surface 25-1 of the mirror 25, the screw 30 is loosened from the outside of the heat conductor 27, and the optical fiber 29 is slidably moved in the longitudinal direction. To detach the optical fiber 29, the screw 30 is loosened from the outside of the heat conductor 27, and the optical fiber 29 is pulled from the rear side of the communicating hole 27g.

In this embodiment, since the thick portion 27c is formed under the inclined surface 27b, the angle of the mirror surface 25-1 does not change even when small vibration or external force is applied. Hence, any adverse effect on the detection accuracy can be prevented.

In this embodiment, since the thick portion 27c is formed under the inclined surface 27b, the volume of the heat conductor 27 near the contact to the thermoelectric cooling element 2 is large. For this reason, the cooling capability (heat exhausting capability) can be increased while implementing size reduction of the sensor.

In this embodiment, the thick portion 27c in which the substance contained in the heat conductor 27 is present is arranged in the space Z1 (FIG. 17) under the inclined surface 27b. However, the substance contained in the heat conductor 27 need not always fill the entire space Z1, and a small gap may be formed. The substance contained in the heat conductor 27 may be present outside the space Z1. In the present invention, even such a state is also defined as the state in which the substance contained in the heat conductor 27 is present in the space Z1.

In this embodiment, the chamber 27m including the inclined surface 27b at the distal end portion 27a of the heat conductor 27 is formed by cutting. However, the chamber 27m need not always be formed by cutting. The entire heat conductor 27 may be formed by using a mold or the like. In this embodiment, the heat conductor 27 is made of copper so that the chamber 27m can easily be formed by cutting. In addition, cutting is suitable for small production, and the cost can consequently be reduced. The heat conductor 27 need not always be made of copper, and for example, aluminum may be used.

Fourth Embodiment: L-Type

FIG. 23 shows the structure of a mirror surface cooling sensor in still another embodiment (fourth embodiment) of a mirror surface cooling dew point detector which uses a thermoelectric device according to the present invention. In the present invention, a mirror surface cooling sensor 205C having the structure shown in FIG. 23 will be referred to as an L-type mirror surface cooling sensor. The L-type mirror surface cooling sensor 205C is connected to a control unit 205B to form a mirror surface cooling dew point detector 205, like the S-type mirror surface cooling sensor 205A of the third embodiment. The same reference numerals as in FIG. 14 denote the same or similar constituent elements in FIG. 23, and a description thereof will be omitted.

Figure 24:
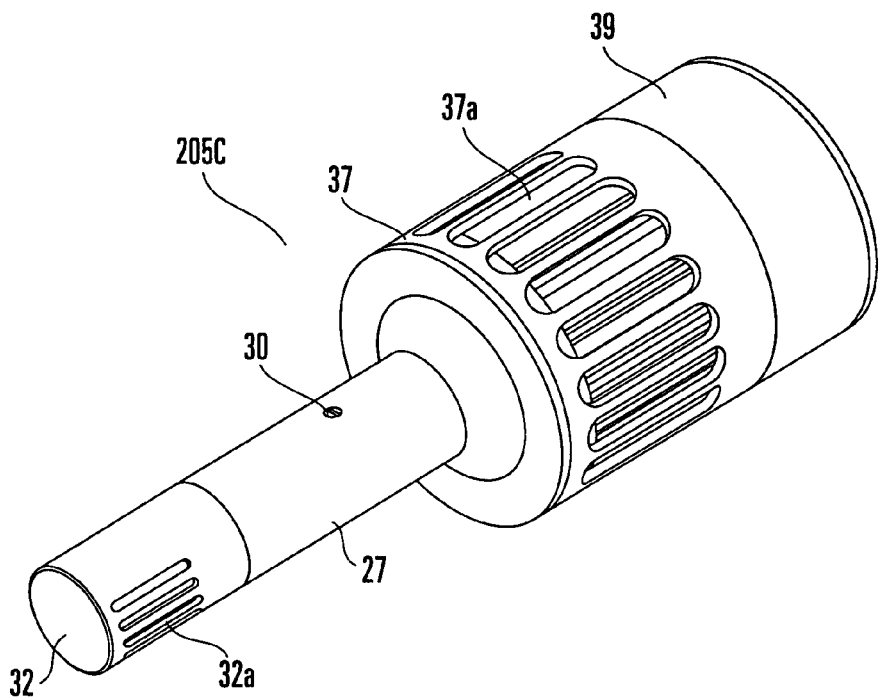
FIG. 24 is a perspective view showing the L-type mirror surface cooling sensor having a mirror cover attached to the detection unit.

The L-type mirror surface cooling sensor 205C has the same basic structure as the S-type except the structure of a radiating portion. In the S-type mirror surface cooling sensor 205A, the semicircular recessed portions 27j are formed behind the trunk 27d of the heat conductor 27, thereby forming the radiating portion 27k. In the L-type mirror surface cooling sensor 205C, however, a large-diameter radiating fin 27p is integrally formed behind of a trunk 27d of a heat conductor 27. The radiating fin 27p is covered with a fin cover 37. As shown in FIG. 24, vent holes 37a are provided in the side surface of the fin cover 37.

Figure 25:
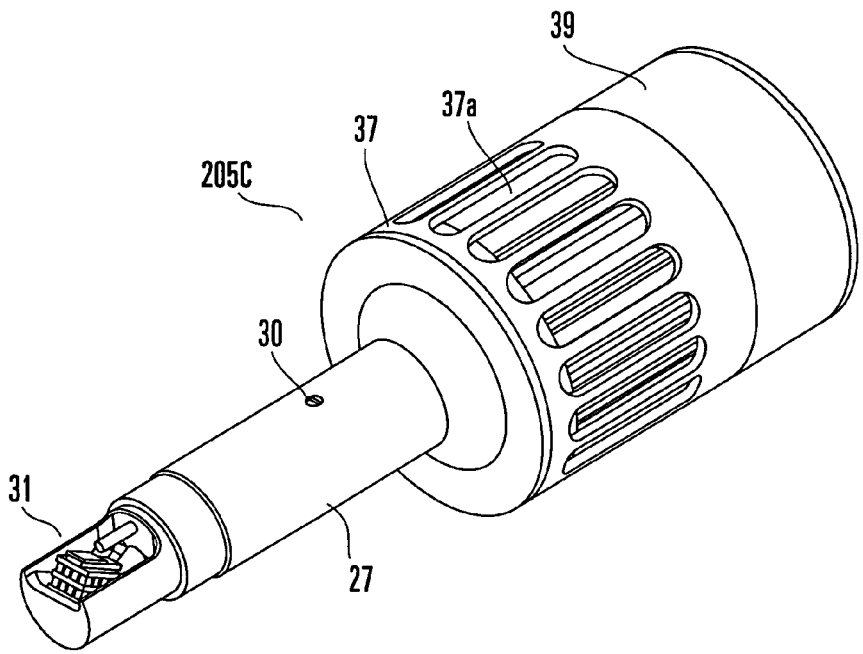
FIG. 25 is a perspective view showing the L-type mirror surface cooling sensor before the mirror cover is attached.
Figure 26:
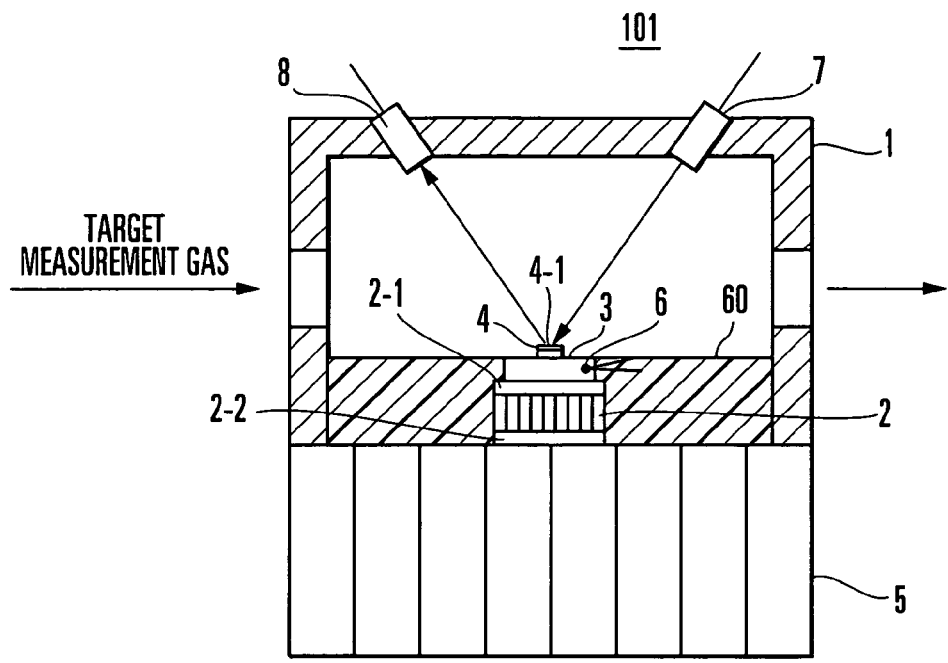
FIG. 26 is a view showing the main part of a conventional mirror surface cooling dew point detector which employs the regular-reflected light detection method.
Figure 27:
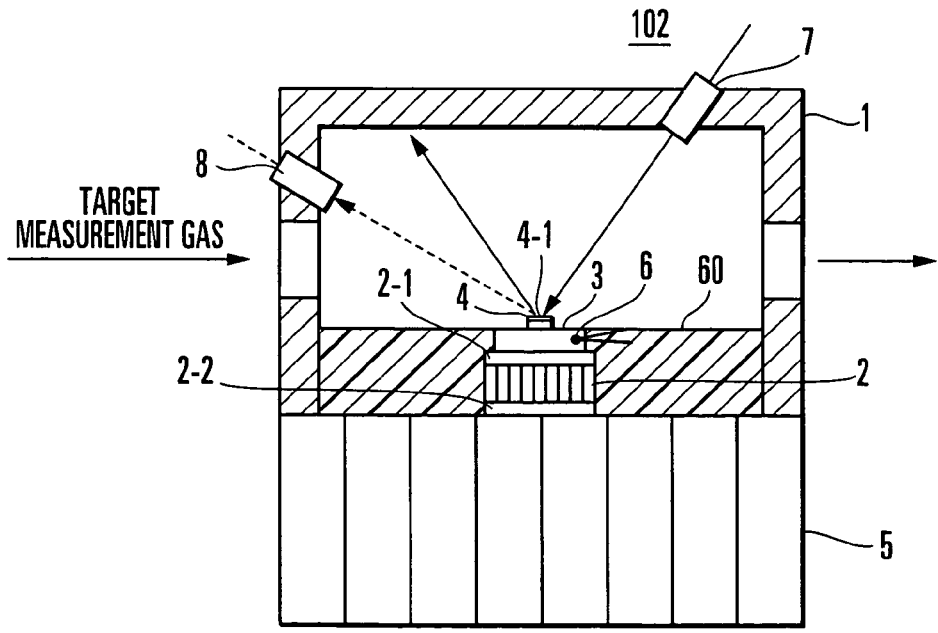
FIG. 27 is a view showing the main part of another conventional mirror surface cooling dew point detector which employs the scattered light detection method.

In addition, a cooling fan 38 is provided behind the radiating fin 27p. A fan cover 39 is attached to the rear portion of the cooling fan 38. A plurality of vent holes 39a are formed in the fan cover 39. A through hole 27p1 in which a lead wire 28 to a thermoelectric cooling element 2 and a fiber line 40 to an optical fiber 29 are inserted is provided at the central portion of the radiating fin 27p. A wire hole in which the lead wire 28 to the thermoelectric cooling element 2, the fiber line 40 to the optical fiber 29, and a lead wire 141 to the fan 38 are inserted is formed in the fin cover 37. FIG. 25 shows the mirror surface cooling sensor 205C before a mirror cover 32 is attached. As is apparent from FIG. 25, the structure of a detection unit 31 is the same as in the S-type mirror surface cooling sensor 205A. The dew point temperature is measured on the basis of the same principle as the S-type.

In the L-type mirror surface cooling sensor 205C, the large-diameter radiating fin 27p is integrally formed behind the trunk 27d of the heat conductor 27. The cooling fan 38 rotates behind the radiating fin 27p. By rotation of the cooling fan 38, outside cool air is drawn into the fan cover 39 through the vent holes 39a of the fan cover 39. This air passes through the spaces in the radiating fin 27p and is forcibly exhausted from the vent holes 37a of the fin cover 37. With this operation, the radiating fin 27p in the fin cover 37 is forcibly cooled, the radiation efficiency increases, and the cooling performance is increased.

Referring to FIG. 23, the fin cover 37, cooling fan 38, and fan cover 39 may be removed.

Figure 21:
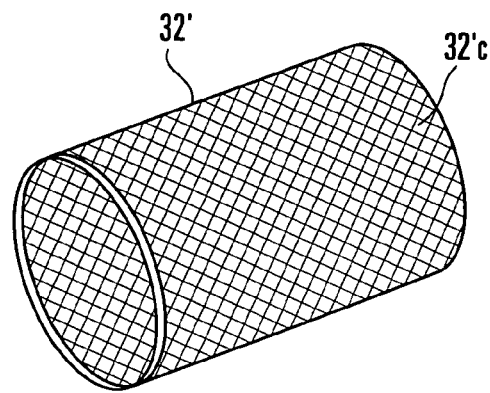
FIG. 21 is a perspective view showing a cover made of a sintered metal.
Figure 22:
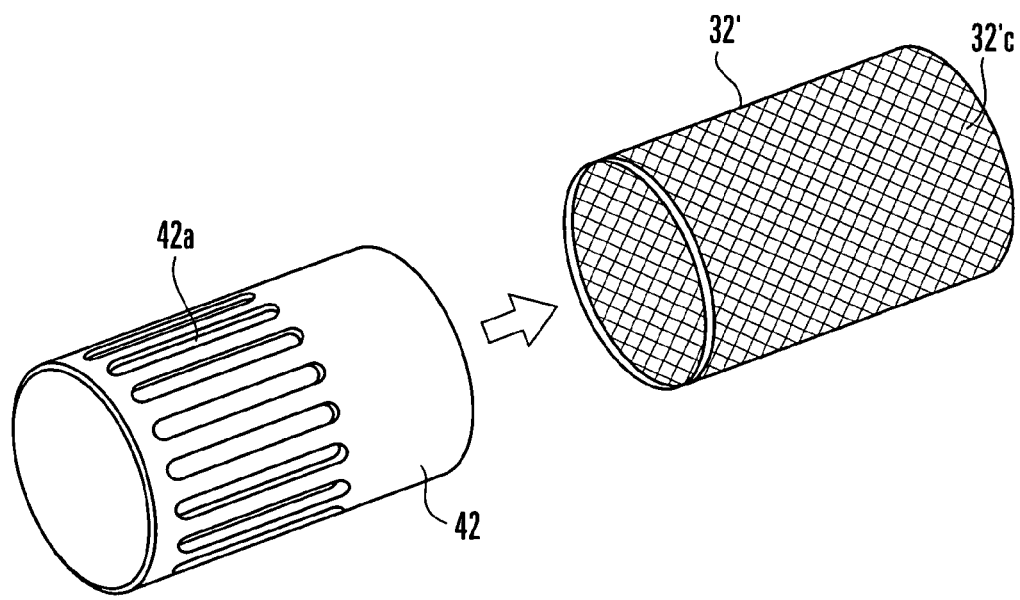
FIG. 22 is a perspective view showing an example in which the cover made of a sintered metal is covered with a protective cover.

Even in the fourth embodiment, a cover 32' made of a sintered metal as shown in FIG. 21 may be used, or the cover 32' made of the sintered metal may be covered with a protective cover 42 as shown in FIG. 22, as in the third embodiment.

In the third and fourth embodiments, the sintered metal is used as the member having the light-shielding effect and ventilation property. However, the member having the light-shielding effect and ventilation property is not limited to the sintered metal.

According to the thermoelectric device of the present invention, the temperature detection element is provided between the cooled member and the low-temperature-side surface of the thermoelectric element or between the heated member and the high-temperature-side surface of the thermoelectric element. For this reason, the thermal resistance is low so that the temperature of the cooled member or heated member can be measured accurately at a high response.

What is claimed is:

1. A thermoelectric device comprising:
a thermoelectric element which has one surface on a low temperature side and the other surface on a high temperature side;
a member which is attached to at least one of the low-temperature-side surface and high-temperature-side surface of said thermoelectric element; and
a temperature detection element which is provided between said member and the surface of said thermoelectric element to which said member is attached, wherein
said member comprises a mirror whose surface opposite to a mirror surface is attached to the low-temperature-side surface of said thermoelectric element, and
the device further comprises
light-emitting means for irradiating the mirror surface of said mirror with pulse light at a predetermined period,
light-receiving means for receiving reflected light of the pulse light emitted from said light-emitting means to the mirror surface, and
means for detecting moisture generated on the mirror surface of said mirror cooled by said thermoelectric element, on the basis of a difference between an upper limit value and lower limit value of one pulse of the reflected light received by said light-receiving means,
a tube having a distal end portion thereof curved so as to have generally a J-shape and direct a tip of the distal end portion to said mirror;
wherein said light-emitting means and said light-receiving means comprise a light-emitting side optical fiber and a light-receiving side optical fiber, respectively, that are both housed in said tube in parallel with each other.

2. A device according to claim 1, wherein
the device further comprises control means for controlling a cooled amount of said mirror by said thermoelectric element on the basis of a state of moisture on the mirror surface detected by said detection means,
a sensor body which accommodates said mirror, said thermoelectric element, said light-emitting means, and said light-receiving means, and
a housing which accommodates said detection means and said control means,
said sensor body being mounted in said housing while exposing at least the mirror surface of said mirror to outside air.

3. A device according to claim 1, wherein
the device further comprises
control means for controlling a cooled amount of said mirror by said thermoelectric element on the basis of a state of moisture on the mirror surface detected by said detection means,
a sensor body which accommodates said mirror, said thermoelectric element, said light-emitting means, and said light-receiving means, and
a housing which accommodates said detection means and said control means,
said sensor body being detachably mounted in said housing while exposing at least the mirror surface of said mirror to outside air.

* * * * *

UNITED STATES PATENT AND TRADEMARK OFFICE
CERTIFICATE OF CORRECTION

| | | |
|---|---|---|
| PATENT NO. | : 7,736,051 B2 | Page 1 of 1 |
| APPLICATION NO. | : 11/097696 | |
| DATED | : June 15, 2010 | |
| INVENTOR(S) | : Yoshiyuki Kanai et al. | |

It is certified that error appears in the above-identified patent and that said Letters Patent is hereby corrected as shown below:

On the Title Page, in Item [30], under Foreign Application Priority Data, at line 3, delete "Oct. 20, 2004" and insert -- Oct. 29, 2004 --.

Signed and Sealed this
Twenty-sixth Day of July, 2011

David J. Kappos
*Director of the United States Patent and Trademark Office*